US011260071B2

(12) United States Patent
Diacovo

(10) Patent No.: US 11,260,071 B2
(45) Date of Patent: Mar. 1, 2022

(54) METHOD OF PREVENTING OF SYSTEMIC-TO-PULMONARY-ARTERY SHUNT THROMBOSIS

(71) Applicant: Chiesi Farmaceutici S.p.A., Parma (IT)

(72) Inventor: Thomas Diacovo, Larchmont, NY (US)

(73) Assignee: Chiesi Farmaceutici S.p.A., Parma (IT)

( * ) Notice: Subject to any disclaimer, the term of this patent is extended or adjusted under 35 U.S.C. 154(b) by 31 days.

(21) Appl. No.: 16/609,800

(22) PCT Filed: Jun. 22, 2018

(86) PCT No.: PCT/EP2018/066817
§ 371 (c)(1),
(2) Date: Oct. 31, 2019

(87) PCT Pub. No.: WO2018/234565
PCT Pub. Date: Dec. 27, 2018

(65) Prior Publication Data
US 2020/0054662 A1 Feb. 20, 2020

Related U.S. Application Data

(60) Provisional application No. 62/524,102, filed on Jun. 23, 2017.

(51) Int. Cl.
| | | |
|---|---|---|
| *A01N 43/04* | (2006.01) | |
| *A61K 31/70* | (2006.01) | |
| *A61K 31/7076* | (2006.01) | |
| *A61P 7/02* | (2006.01) | |
| *A61K 9/00* | (2006.01) | |

(52) U.S. Cl.
CPC ........ *A61K 31/7076* (2013.01); *A61K 9/0019* (2013.01); *A61K 9/0053* (2013.01); *A61P 7/02* (2018.01)

(58) Field of Classification Search
None
See application file for complete search history.

(56) References Cited

U.S. PATENT DOCUMENTS

| | | |
|---|---|---|
| 4,529,596 A | 7/1985 | Aubert et al. |
| 5,196,404 A | 3/1993 | Maraganore et al. |
| 5,288,726 A | 2/1994 | Koike et al. |
| 5,721,219 A | 2/1998 | Ingall et al. |
| 5,955,447 A | 9/1999 | Ingall et al. |
| 6,114,313 A | 9/2000 | Bland et al. |
| 6,130,208 A | 10/2000 | Broadhead |
| 6,693,115 B2 | 2/2004 | Asai et al. |
| 6,861,424 B2 | 3/2005 | Bryant et al. |
| 7,026,323 B2 | 4/2006 | Bryant et al. |
| 8,680,052 B1 * | 3/2014 | Arculus-Meanwell ..................... A61K 47/02 514/14.7 |
| 8,716,261 B2 | 5/2014 | Ruderman Chen et al. |
| 8,871,736 B2 | 10/2014 | Ruderman Chen et al. |
| 9,427,448 B2 | 8/2016 | Arculus-Meanwell et al. |
| 9,925,265 B2 | 3/2018 | Arculus-Meanwell et al. |
| 2002/0123791 A1 | 9/2002 | Harrison |
| 2006/0121086 A1 | 6/2006 | Boyer et al. |
| 2006/0270607 A1 | 11/2006 | Dixon et al. |
| 2007/0082840 A1 | 4/2007 | Porter et al. |
| 2007/0254324 A1 | 11/2007 | Rechner |
| 2007/0276460 A1 | 11/2007 | Davis et al. |
| 2009/0043380 A1 | 2/2009 | Blaha et al. |
| 2009/0048216 A1 | 2/2009 | Gretler et al. |
| 2009/0088834 A1 | 4/2009 | Wang |
| 2009/0247465 A1 | 10/2009 | Baldo et al. |
| 2009/0304770 A1 | 12/2009 | Lewis et al. |
| 2010/0041587 A1 | 2/2010 | Porter et al. |
| 2010/0120718 A1 | 5/2010 | Perzborn |
| 2010/0292268 A1 | 11/2010 | Mosher et al. |
| 2011/0112030 A1 | 5/2011 | Arculus-Meanwell et al. |
| 2011/0178594 A1 | 7/2011 | Kim et al. |
| 2011/0276123 A1 | 11/2011 | Davies et al. |
| 2011/0288043 A1 | 11/2011 | Chen et al. |
| 2012/0009172 A1 | 1/2012 | Gretler et al. |
| 2012/0141468 A1 | 6/2012 | Chen et al. |
| 2012/0184504 A1 | 7/2012 | Stony et al. |
| 2013/0040898 A1 | 2/2013 | Johansson |
| 2013/0190265 A1 | 7/2013 | Arculus-Meanwell et al. |
| 2013/0324492 A1 | 7/2013 | Chen et al. |
| 2013/0303477 A1 | 11/2013 | Chen et al. |
| 2013/0303478 A1 | 11/2013 | Chen et al. |
| 2013/0316968 A1 | 11/2013 | Chen et al. |
| 2014/0107032 A1 | 4/2014 | Arculus-Meanwell et al. |
| 2015/0038449 A1 | 2/2015 | Chen et al. |

FOREIGN PATENT DOCUMENTS

| | | |
|---|---|---|
| CN | 103860459 A | 6/2014 |
| EP | 2105137 A1 | 9/2009 |
| EP | 2672975 A1 | 12/2013 |
| WO | 199418216 A1 | 2/1994 |
| WO | 200139781 A1 | 6/2001 |
| WO | 2005097814 A2 | 10/2005 |
| WO | 2006119507 A2 | 11/2006 |
| WO | 2007024472 A2 | 3/2007 |
| WO | 2008052671 A3 | 7/2008 |
| WO | 2008127682 A2 | 8/2008 |
| WO | 2009140092 A1 | 11/2009 |
| WO | 2011060066 A2 | 5/2011 |
| WO | 2011134478 A2 | 11/2011 |
| WO | 2012109406 A1 | 8/2012 |
| WO | 2013025476 A1 | 2/2013 |
| WO | 2016114818 A1 | 7/2016 |
| WO | 2016035780 A1 | 10/2016 |

OTHER PUBLICATIONS

Mohanty et al. Ann. Pediatr. Cardiol. (2013), vol. 6 (1), pp. 59-64.*
Heidari-Bateni G, Norouzi S, Hall M, Brar A, Eghtesady P. Defining the best practice patterns for the neonatal systemic-to-pulmonary artery shunt procedure. J Thorac Cardiovasc Surg. Mar. 2014;147(3):869-873.e3. doi: 10.1016/.jtcvs.2013.10.063. Epub Dec. 9, 2013.

(Continued)

*Primary Examiner* — Patrick T Lewis
(74) *Attorney, Agent, or Firm* — Vorys, Sater, Seymour and Pease LLP; Maryellen Feehery Hank

(57) ABSTRACT

The present invention is directed to the use of cangrelor for the treatment and/or prevention of shunt thrombosis in patients suffering congenital heart diseases undergoing shunt surgery. The invention is also directed to the use of cangrelor for the treatment and/or prevention of stent thrombosis in pediatric patients undergoing stent implantation.

22 Claims, 7 Drawing Sheets

(56) References Cited

OTHER PUBLICATIONS

Figure 1:
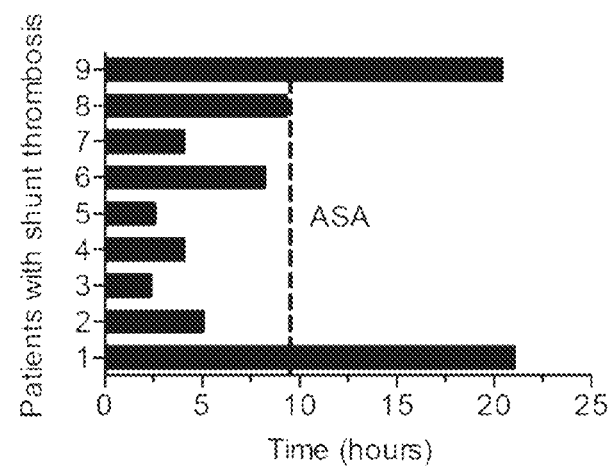

A. Siddique et al.: "New antiplatelet drugs: beyond aspirin and clopidogrel"; International Journal of Clinical Practice vol. 64, No. 5, May 1, 2009 (May 1, 2009); pp. 776-789, XP055506219, GB; ISSN: 1368-5031, DOI: 10.1111/.1742-1241.2009.02058.x; Cangrelor; p. 784, right-hand column—p. 785, left hand column.

Monagle et al.: "Thrombosis in children with BT shunts, Glenns and Fontans"; Progress in Pediatric Cardiology Elsevier, Amsterdam, NL; vol. 21, No. 1; Dec. 1, 2005; (Dec. 1, 2005); pp. 17-21; XP027631662; ISSN 1058-9813; Retrieved on Dec. 1, 2005—the whole document.

Monagle P, Newall F, Barnes C, Savoia H, Campbell J, Wallace T, Crock C. Arterial thromboembolic disease: a single-centre case series study J. Paediatr Child Health. 2008; 44:28-32.

Formene D, Gavasso S, Rossetto V, Simioni P.; Thrombosis and thrombophilia in children: a systematic review. Semin Throm. Hemost. 2006; 32:724-728.

Manlhiot C, Menjak IB, Brandao LR, Greenwald CE, Schwartz SM, Sivarajan VB, Yoon H, Maratta R, Carew CL, McMullen JA, Clarizia NA, Holtby HM, Williams S, Caldarone CA, Van Arsdell GS, Chan AK, McCrindle BW. Risk, clinical features, and outcomes of thrombosis associated with pediatric cardiac surgery. Circulation 2011 124:1511-1519.

Chalmers EA. Neonatal thrombosis. J Clin Pathol. 2000; 53:419-423.

Reed RC, Rutledge JC. Laboratory and clinical predictors of thrombosis and hemorrhage in 29 pediatric extracorporeal membrane oxygenation nonsurvivors. Pediat Dev Pathol. 2610; 13:385-392.

Monagle P. Anticoagulation in the young. Heart 2004; 90:808-812.

Fenton KN, Siewers RD, Rebovich B. Pigula FA. Interim mortality in infants with systemic-to pulmonary artery shunts. Ann Thorac Surg 2003; 76:152-156.

Pahl E, Naftel DC, Kuhn MA, Shaddy RE, Morrow WR, Canter CE, Kirklin J. The impact and outcome of transplant coronary artery disease in a pediatric population: a 9-year multi-institutional study. J Heart Lung Transplant 2005 24:645-651.

Al Jubair KA; Al Fagih MR, Al Jarallah AS, Al Yousef S, Ali Khan MA, Ashmeg A; Al Faraidi Y, Sawyer W. Results of 546 Blalock-Taussig shunts performed in 478 patients. Cardiol Young. 1998; 8:486-490.

Turner ME, Addonizio LI, Richmond ME, Zuckerman WA, Vincent JA, Torres AJ, Collins MB. Percutaneous coronary artery revascularization procedures in pediatric heart transplant recipients: A large single center experience Catheter Carchovasc interv. 2016.

Li JS, Yow E, Berezny KY, Rhodes IF, Bokesch PM, Charpie JR, Forbus GA, Mahony L, Boshkov L, Lambert V, 3onnet D, Michel-Behnke I, Graham TP, Takahashi M, Jaggers J, Califf RM, Rakhit A, Fontecavc S, Sanders SP. Clinical outcomes of palliative surgery including a systemic-to-pulmonary artery shunt in infants with cyanotic congenital heart disease: does aspirin make a difference? Circulation. 2007; 116:293-297.

Motz R, Wessel A, Ruschewski W, Bursch J. Reduced frequency of occlusion of aorto-pulmonary shunts in infants Yeceiving aspirin. Cardiol Young. 1999; 9:474-477.

Levine GN, Bates ER, Blankenship JC, bailey SK, Brittl JA, Cercek B, Chambers CE, Ellis SG, Guyton RA, Hollenberg SM, Khot UN, Lange RA, Mauri L, Mehran R, Moussa ID, Mukherjee D, Nallamothu BK, Ting HH. 2011 ACCF/AHA/SCA1 guideline for percutaneous coronary intervention: a report of the American College of Cardiology Foundation/American Heart Association Task Force on Practice Guidelines and the Society for Cardiovascular Angiography and nterventions. Circulation. 2011; 124:e574-651.

Gurbel PA, Bliden KP, Hiatt BL, O'Connor CM. Clopidogrel for coronary stenting: response variability, drug resistance, and the effect of pretreatment platelet reactivity. Circulation 2004; 107:2908-2913.

Mehta SR, Tanguay JF, Eikelboom JW, Jolly SS, Joyner CD, Granger CB, Faxon DP, Rupprecht HJ, Budaj A, Aveaum A, Widimsky P, Steg PG, Bassnad JP, Montalescot G, Macaya C, Di Pasquale G, Niemela K, Ajani AE, White HD, Chrolavicius S, Gao P, Fox KA, Yusuf S. Double-dose versus standard-dose clopidogrel and high-dose versus low-Tose aspirin in individuals undergoing percutaneous coronary intervention for acute coronary syndromes (CURRENT-PASIS 7): a randomised factorial trial Lancet 2010; 376:1233-1243.

Steinhubl SR, Berger PB, Mann JT 3rd, Fry ET, DeLago A, Wilmer C, Topol Ej; Credo Investigators. Clopidogrel for he Reduction of Events During Observation. Early and sustained dual oral antiplatelet therapy following percutaneous coronary intervention: a randomized controlled trial. JAMA. 2002 288:2411-2420.

Dorsam RT, Kunapuli SP Central role of the P2Y12 receptor in platelet activation. J Clin Invest 2004; 113:340-345.

Cattaneo M. P2Y12 receptors: structure and function. J Thromb Haemost. 2015;13 Suppl 1: S10-6.

Cattaneo M. Update on Antithrombotic Therapy. New P2Y12 Inhibitors. Circulation 2010; 121: 171-179.

Franchi F, Angiolillo DJ. Novel antiplatelet agents in acute coronary syndrome. Nature Reviews Cardiology. 2015 12:30-47.

Wessel DL, Berger F, Li JS, Dahnert I, Rakhit A, Fontecave S, Newburgcr JW for the Clarinet Investigators. Clopidogrel in infants with systemic-to-pulmonary-artery shunts. N Engl J Med. 2013; 368 2377-2384.

Li JS, Yow E, Berezny KY, Bokesch PM, Takahashi M, Graham TP Jr, Snaders SP, Sidi D, Bonnet D, Ewert P, Jennings LK, Michelson AD. Dosing of clopidogrel for platelet inhibition in infants and young children: primary results of the Platelet Inhibition in Children On cLOpidogrel (PICOLO) trial. Circulation. 2008, 117:553-559.

Akers WS, Oh JJ, Oestreich Jl-I, Ferraris S, Wethington M, Steinhubl SR. Pharmacokinetics and pharmacodynamics of a bolus and infusion of cangrelor: a direct, parenteral P2Y12 receptor antagonist...J Clin Pharmacol- 2010; 50:27-35.

Van Giezen JJJ, Humphries RC. Preclinical and clinical studies with selective reversible direct P2Y12 antagonists. Semin Thromb Hemost. 2005; 31:195-204.

Marino M, Rizzotti D, Leonardi S. Cangrelor: review of the drug and the CHAMPION programme (including PHOENIX). Durr Cardiol Rep 2014; 16.493.

White HD, Chew DP, Dauerman HL, Mahaffey KW, Gibson CM, Stone GW, Gruberg L, Harrington RA, Bhatt DL. Reduced immediate ischemic events with cangrelor Am Heart J 2012; 163:182-190.

Bhatt DL, Stone GW, Mahaffey KW, Gibson CM, Steg PG, Hamm CW, Price MJ, Leonardi S, Gallup D, Bramucci E, Radke PW, Widimsky P, Tousek F, Touth J, Spriggs D, McLaurin BT, Angiolillo DJ, Genereux P, Liu T, Prats J, Todd M, Skerjanec S, White HD, Harrington RA. Effect of platelet inhibition with cangrelor during PCI on ischemic events N Engl J Med 2013; 368:1303-1313.

Angiolillo DJ, Firstenberg MS, Price MJ, Tummala PE, Hutyra M, Welsby IJ, Voeltz MD, Chandna H, Ramaiah C, Brtko M, Cannon L, Dyke C, Liu T, Montalescot G, Manoukian SV, Prats J, Topol EJ. Bridging antiplatelet therapy with cangrelor in patients undergoing cardiac surgery: a randomized controlled trial. JAMA 2012; 307. 265-274.

Dhen JC, Zhou H, Diacovo A, Zheng XL, Emsley J, Diacovo TG. Exploiting the kinetic interplay between the GPIba—VWF binding interfaces to regulate hemostasis and thrombosis Blood. 2014; 124:3799-3807.

Doggett TA, Girdhar G, Lawshe A, Schmidtke DW, Laurenzi IJ, Diamond SL, Diacovo TG. Selectin-like kinetics and biomechanics promote rapid platelet adhesion in flow: the GPIba-vWF tether bond. Biophys J 2002; 83:194-205.

Chen JC, Tan K, Zhao H, Tronik-Le Roux D, Liddington RC, Diacovo LG. Modifying murine von Willebrand Factor Al domain to permit in vivo assessment of human platelet therapies. Nat Biotech 2008; 26. 114-119.

Li R, Diamond SL. Detection of platelet sensitivity to inhibitors of COX-1, P2Y1, and P2Y12 using a whole blood microfluidic flow assay. Thrombosis Res 2013; 133:203-210.

(56) References Cited

OTHER PUBLICATIONS

Magallon J, Chen JC, Rabbani L, Dangas G, Yang J, Bussel J, Diacovo T. Humanized mouse model of thrombosis is predictive of the clinical efficacy of antiplatelet agents. Circulation 2011; 123:319-326.
Bagiella E, Sloan RP, Heitjan DF. Mixed-effects models in psychophysiology. Psychophysiology. 2000; 37:13-20.
Rajasekhar D, Kestin AS, Bednarek FJ, Ellis PA, Barnard MR, Michelson AD. Neonatal platelets are less reactive than adult platelets to physiological agonists in whole blood. Thromb Haemost; 1994; 72:957-963.
Mull MM, Hathaway WE. Altered platelet function in newborns, Pecliatr Res. 1970; 4:229-237.
Ware JA, Reaves WH, Horak JK, Solis RT. Defective platelet aggregation in patients undergoing surgical repair of cyanotic congenital heart disease Am Thorac Surg. 1983; 36:289-94.
Kierzkowska B, Staticayk J, Wiectawska B, Rozalski M, Bonder Ni, Chrul S, Watala C. Activation of circulating platelets and platelet response to activating agents in children with cyanotic congenital heart disease: their relevance to palliative systemic-pulmonary shunt. Int J Cardiol. 2001; 79:49-59.
Storey RF, Oldroyd KG, Wilcox RG. Open muiticentre study of the P2T receptor antagonist AR-C69931 Mx assessing safety, tolerability and activity in patients with acute coronary syndromes Thromb Haemost 2001, 85: 401-407.
Angiolillo DJ, Schneider DJ, Bhatt DL, French WJ, Price MJ, Saucedo JF, Shaburishvili T, Huber K, Prats J, Liu T, Harrington RA, Becker RC. Pharmacodynamic effects of cangrelor and clopidogrel: the platelet function substudy from the cangrelor versus standard therapy to achieve optimal management of platelet inhibition (CHAMPION) trials J. Thromb Thrombolysis. 2012; 34:44-55.
Harrington RA, Stone GW, McNulty S, White HD, Lincoff AM, Gibson CM, Pollack CV Jr, Montalescot G, Mahaffey KW, Kleiman NS, Goodman SG, Amine M, Angiolillo DJ, Becker RC, Chew DP, French WJ, Leisch F, Parikh KH, Skerjanec S, Bhatt DL. Platelet inhibition with cangrelor in patients undergoing PCI. New Eng J Med. 2009 361:2318-2329.
Bhatt DL, Stone GW, Mahaffey KW, Gibson CM, Steg PG, Hamm CW, Price MJ, Leonardi S, Gallup D, Bramucci E, Radke PW, Widimsky P, Tousek F, Tauth J, Spriggs D, McLaurin BT, Angiolillo DJ, Genereux P, Liu T, Prats J, Todd Ml, Skerjanec S, White HD, Harrington RA. Effect of platelet inhibition with cangrelor during PCI on ischemic events N Eng J. Med. 2013, 368:1303-1313.
Trissel L.A. et al., Turbidimetric assessment of the compatibility of taxol with 42 other drugs during simulated Y-site njection Am J. Hosp Pharm 50: 300-4 (1993).
Steinhubl SR, Oh JJ, Oestreich, JH, et al., Transitioning patients from cangrelor to clopidogrel: Pharmacodynamic avidence of a competitive effect, Thromb Res, 2007, pp. 527-534, vol. 121.
Stalker TJ, Traxler EA, Wu J, Wannemacher KM, Cermignano SL, Voronov R, Diamond SL, Brass LF. Hierarchical organization in the hemostatic response and its relationship to the platelet-signaling network. Blood. 2013; 121:1875-1885.
Victor L. Serebruany, Alex L Malinin, Roswith M. Eisert, and David C. Sane. Risk of Bleeding Complications With Antiplatelet Agents: Meta-Analysis of 338,191 Patients Enrolled in 50 Randomized Controlled Trials. American Journal of Hematology. 2004; 75:40-47.
McHugh KE, Hillman DG, Gurka MJ, Gutgesell HP. Three-stage Palliation of Hypoplastic Left Heart Syndrome in the University Healthsystem Consortium. Congenit Heart Dis. 2010; 5.8-15.
Faxon DP, Cangrelorfor ACS lessons from the Champion trials, Nat Rev Cardiol, 2010, pp. 124-125, vol. 7.
Feldman et al., Impact of bivalirudin on outcomes after percutaneous coronary revascularization with drug-eluting stents. American Heart Journal. Oct. 2007. vol. 154, No. 4, pp. 695-701.
Ferreriro JL, et al., Cangrelor: a review on its mechanism of action and clinical development, Expert Rev Cardiovasc Ther, 2009, pp. 1195-1201, vol. 7.

Firstenberg, M.S., et al., Safety and Efficacy of Cangrelor, an Intravenous, Short-Acting Platelet Inhibitor in Patients Requiring Coronary Artery Bypass Surgery, The Heart Surgery Forum, 2013, pp. E60-E69, vol. 16, No. 2.
Fox SC, et al., Effects on platelet function of an EP3 receptor antagonist used alone and in combination with a P2Y12 antagonist both in-vitro and ex-vivo in human volunteers, Platelets, 2013, pp. 392-400, vol. 24, No. 5.
Fugate SE and Cudd LA, Cangrelor for treatment of coronary thrombosis, Ann Pharmacother, 2006, pp. 925-930, vol. 40.
Geisler T, et al., Current strategies in antiplatelet therapy — Does identification of risk and adjustment of therapy contribute to more effective, personalized medicine in cardiovascular disease?, Pharmacol Ther, 2010, pp. 95-107, vol. 127.
Gitt AK, Betriu A., Antiplatelet therapy in acute coronary syndromes, Eur Heart J, 2008, pp. A4-AI2, 10 Supp. A.
Greenbaum AB, et al., Initial experience with an intravenous P2Y12 platelet receptor antagonist in patients undergoing percutaneous coronary intervention: Results from a 2-part, phase II, multicenter, randomized, placebo- and active-controlled trial, Am Heart J, 2006, p. 689.e1- 689.e10.
Greenbaum AB, et al., Intravenous adenosine diphosphate P2T platelet receptor antagonism as an adjunct to fibrinolysis for acute myocardial infarction, JACC, 2002, p. , vol. 39, Issue 5, Supp A.
Greenbaum AB, et al., Preliminary experience with intravenous P2Y12 platelet receptor inhibition as an adjunct to Yeduced-dose alteplase during acute myocardial infarction: Results of the Safety, Tolerability and Effect on Patency in Acute Myocardial Infarction (STEP-AMI) angiographic trial, Am Heart J, 2007 pp. 702-709, vol. 54, No. 4.
Gruntzig A.R. et al., Nonoperative dilatation of coronary-artery stenosis: percutaneous transluminal coronary angioplasty, N Engl J Med 301:61-8 (1979).
Gurbel PA et al., The relation of dosing to clopidogrel responsiveness and the incidence of high post-treatment platelet aggregation in patients undergoing coronary stenting. J Am Coll Cardiol 45: 1392-6 (2005).
Gurbel, et al., Oral Dosing of PRT060128, a Novel Direct-Acting, Reversible-P2Y(12) Antagonist Overcomes High Platelet Reactivity in Patients Non-Responsive to Clopidogrel Therapy, Circulation, 2008, p. S972, vol. 118, No. 18.
Gurbel, et al., Peri-Operative Platelet Function Testing: The Potential for Reducing Ischaemic and Bleeding Risks, Thromb. Haemost., 2011, pp. 248-252, vol. 106.
Hall R, et al., Antiplatelet drugs: a review of their pharmacology and management in the perioperative period, Anesthesia & Analgesia, 2011, pp. 292-318, vol. 112, No. 2.
Heestermans et al., Impaired bioavailability of clopidogrel in patients with a ST-segment elevation myocardial nfarction. Thromb Res 2008; 122: 776-81.
Huang J, et al., Prevention of arterial thrombosis by intravenously administered platelet P2T receptor antagonist AR-566931 Mx in a canine model, J Pharmacol Exp Ther, 2000, pp. 492-499, vol. 295, No. 2.
Humphries RG, Pharmacology of AR-C69931MX and related compounds: from pharmacological tools to clinical trials, Haematologica, 2000, pp. 66-72, 85(the Platelet ADP Receptors Supp.).
Ingall AH, et al., Antagonists of the platelet P2T receptor: a novel approach to antithrombotic therapy, J Med Chern, 1999, pp. 213-220, vol. 42.
Ingall AH, P2T receptor antagonists: novel inhibitors of platelet aggregation, Arch Pharm, 1999, pp. 11-12, Supp. 1.
International Conference on Harmonization (ICH) Guidance Documents. U.S. Food and Drug Administration Web site. Accessed on Oct. 8, 2009, at the FDA website beginning with "www." and ending with "fda.gov/Regulatory Information/Guidances/ucm 122049. htm".
International Search Report and Written Opinion by the International Searching Authority, dated Feb. 10, 2015, in the PCT Application No. PCT/US2014/059972.
International Search Report and Written Opinion by the International Searching Authority, dated Jan. 3, 2014, in the PCT Application No. PCT/US2013/048735.

(56) References Cited

OTHER PUBLICATIONS

International Search Report and Written Opinion by the International Searching Authority, dated Jun. 11, 2009, in the PCT Application No. PCT/IJS09/42681.
International Search Report and Written Opinion by the International Searching Authority, dated Jun. 2, 2014, in the PCT Application No. PCT/US2013/048741.
International Search Report and Written Opinion by the International Searching Authority, dated Jun. 30, 2009, in the PCT Application No. PCT/IJS09/43820.
Iyu D, et al., Adenosine derived from ADP can contribute to inhibition of platelet aggregation in the presence of a P2Y12 antagonist, Arterioscler Thromb Vase Biol, 2011, pp. 416-422, vol. 31.
Iyu D, et al., Mode of action of P2Y12 antagonists as inhibitors of platelet function, Thromb Haemost, 2011, pp. 96-105, vol. 105.
Jacobsson F, et al., JACC, 2000, p. 343, vol. 35, Issue, 2, Supp. A.
Jacobsson F, et al., Safety profile and tolerability of intravenous AR C69931MX, a new antiplatelet drug, in unstable angina pectoris and non Q wave myocardial infarction, Clin Ther, 2002, pp. 752-765, vol. 24, No. 5.
Jarvis GE, et al., Superior inhibition of ADP induced human platelet aggregation by AR C69931MX than clopidogrel, Drug Dev Res, 2000, p. 90. vol. 50, No. 1.
Jarvis GE, et al., The P2T antagonist AR C69931MX is a more effective inhibitor of ADP induced platelet aggregation than clopidogrel, Blood, 1999, p. 194, (10 Supp pt. 1):22a.
Judge HM, et al., Glycoprotein Ith/llla and P2Y12 receptor antagonists yield additive inhibition of platelet aggregation, granule secretion, soluble CD40L release and procoagulant responses, Platelets, 2005, pp. 398-407, vol. 16, No. 7.
Kandzari DE, Evolving antithrombotic treatment strategies for acute ST-elevation myocardial infarction, Rev Cardiovasc Med, 2006, pgs. S29-S37, vol. 7, Supp. 4.
King S.B. 3rd. et al., 2007 Focused Update of the ACCIAHA/SCAI 2005 Guideline Update for Percutaneous Coronary Intervention: a report of the American College of Cardiology/American Heart Association Task Force on Practice Guidelines: 2007 Writing Group to Review New Evidence and Update the ACCIAHA/SCAI 2005 Guideline Update for Percutaneous Coronary Intervention, Writing on Behalf of the 2005 Writing Committee. Circulation 117:261-95(2008).
Krajewski, S., et al., Short-acting P2Y12 blockade to reduce platelet dysfunction and coagulopathy during experimental axtracorporeal circulation and hypothermia, BJA, 2012, pp. 912-921, vol. 108, No. 6.
Kuijpers MJ, et al., Regulation of tissue factor-induced coagulation and platelet aggregation in flowing whole blood, Thromb Haemost, 2005; 93, pp. 97-105.
Kunapuli SP, et al., ADP receptors target for developing antithrombotic agents, Curr Pharm Des, 2003, vol. 9, pp. 2303-2316.
Lehman and Chew, "Bivalirudin in percutaneous coronary intervention", Vascular Health and Risk Management, 2006, pp. 357-363.
Leon C, et al., Platelet ADP receptors contribute to the initiation of intravascular coagulation, Blood, 2004, pp. 594-600, vol. 103, No. 2.
Leonardi S, et al., A novel approach to systematically implement the universal definition of myocardial infarction insights from the Champion Platform trial, Heart, 2013, pp. 1282-1287, vol. 99.
Leonardi S, et al., A novel approach to implement the universal definition of myocardial infarction in patients undergoing very early invasive management: insights from the CHAMPION Platform trial, AHA Orlando, FL, Nov. 12-16, 2011.
Leonardi S, et al., Maintenance therapy with thienopyridines may reduce enzymatic infarct size in patients with acute coronary syndrome undergoing PCI: Insights form the Champion PCI trial AHA Chicago, IL, 2010.
Leonardi S, et al., Pre-treatment with thienopyridines reduces the amount of myonecrosis in acute coronary syndrome patients invasively managed, insights from the CHAMPION trials, Circulation, 2010, pg. A14813, vol. 122, No. 21, Suppl. S.
Leonardi S, et al., Rationale and design of the cangrelor versus standard therapy to achieve optimal management of platelet inhibition PHOENIX trial, Am Heart J, 2012, pp. 768-776.e2, vol. 163.
Lepantalo A, et al., Antiplatelet Effect of Clopidogrel in Patients with Aspirin Therapy Undergoing Percutaneous Coronary Interventions—Limited Inhibition of the P2Y12 Receptor, Thromb. Res., 2009, pp. 193-198, vol. 124, No. 2.
Lincoff et al. Bivalirudin with planned or provisional abciximab versus low-dose heparin...American Heart Journal, May 2002, vol. 143, No. 5, pp. 847-853.
Mahaffey KW et al., Misreporting of myocardial infarction end points: results of adjudication by a central clinical events committee in the Paragon-B trial. Second Platelet llb/llla Antagonist for the Reduction of Acute Coronary Syndrome Events in a Global Organization Network Trial. Am Heart J 143:242-8 (2002).
Maisel WH, Unanswered Questions-Drug-Eluting Stents and the Risk of Late Thrombosis N Engl J Med 356:981-4 [2007].
Mazzucato M, et al., Crucial role of the ADP receptor P2Y1 in platelet adhesion and signaling under high flow, Blood, 2002, p. 100,11.
Meadows TA, et al., Clinical aspects of platelet inhibitors and thrombus formation, Circ Res 100:1261-75 (2007).
Mega JL, et al., Cytochrome p-450 polymorphisms and response to clopidogrel, N Engl J Med 360:354-62 (2009).
Leonardi S., et al., Pre-treatment with thienopyridines reduces the amount of myonecrosis in acute coronary syndrome patients invasively managed: insights from the CHAMPION Trials, Circulation, 2010, pg. AI4813, vol. 122, No. 21, Suppl S.
Mehta SR, et al., Routine vs selective invasive strategies in patients with acute coronary syndromes: a collaborative meta-analysis of randomized trials, JAMA 2005; 293:2908-17.
Michelson AD, P2Y12 Antagonism. Promises and challenges, Arterioscler Thromb Vase Biol, 2008, pp. S33-S38.
Murugappan S and Kunapuli S, The role of ADP receptors in platelet function, Front Biosci, 2006, pp. 1977-1986, vol. 11.
Nassim MA, et al., Investigation of the novel P2T receptor antagonist AR C69931MX on ex vivo adenosine diphosphate induced platelet aggregation and bleeding time in healthy volunteers, JACC, 1999, p. 33, vol. 33 (Supp A).
NCT00305162 Clinical Trials.gov Archive, https://clinicaltrials.gov/ct2/archive/NCT00305162, May 19, 2009.
NCT00767507 Clinical Trials.gov Archive, https://clinicaltrials.gov/archive/NCT00767507/2008, Oct. 6, 2008.
Niitsu Y, et al., Pharmacology of CS-747 (Prasugrel, LY640315), a novel, potent antiplatelet agent with in vivo P2Y12 Yeceptor antagonist activity, Semin Thromb Hemost, 2005, pp. 184-194, vol. 31, No. 2.
Nogard NB and Abu-Fadel M, Future prospects in anti-platelet therapy: A review of potential P2Y12 and thrombin Yeceptor antagonists, Recent Patents Cardiovasc Drug Discovery, 2008, pp. 194-200, vol. 3.
Norgard NB, Cangrelor: a novel P2Y12 receptor antagonist, Expert Opin Investig Drugs, 2009, pp. 1219-1230, vol. 18.
Nurden AT and Nurden P, Advantages of fast-acting ADP receptor blockade in ischemic heart disease (Editorial to K. Wang article p. 357), Arterioscler Thromb Vase Biol, 2003, pp. 158-159.
Nylander S, et al., Characterization of species differences in the platelet ADP and thrombin response, Thromb Res, 2003, pp. 65-73, vol. 111.
Oestreich JH, Steinhubl SR, Cangrelor in percutaneous coronary intervention, Expert Rev Clin Pharmacol, 2009, pp. 137-145, vol. 2.
Destrich, JH and Dobesh, PP, Cangrelor for treatment during percutaneous coronary intervention, Future Cardiology, 2014, 10(2), 201-213.
Office Action dated Jun. 11, 2013 in the related Japanese Application No. 2011-509659.
Office Action dated Jun. 30, 2015 in the related European Application No. 09747490.2.

(56) References Cited

OTHER PUBLICATIONS

Office Action dated Jun. 4, 2013 in the related Chinese Application No. 200980126678.1.
Oliphant CS, et al., Emerging P2Y12 receptor antagonists:role in coronary artery disease, Curr Vase Pharmacol, 2010, pp. 93-101, vol. 8.
Paikin JS, et al., New antithrombotic agents-insights from clinical trials, Nat Rev Cardiol, 2010, pp. 498-509, vol. 7.
Park SJ and Lee SW, Optimal management of platelet function after coronary stenting, Cur Treat Options Cardiovasc Med, 2007, pp. 37-45.
Parravicini C, et al., GPR17: Molecular modeling and dynamics studies of the 3-D structure and purinergic ligand binding features in comparison with P2Y receptors, BMC Bioinformatics, 2008, pp. 1-19, vol. 9, No. 263.
Penz SM, et al., Glycoprotein Iba inhibition and ADP receptor antagonists, but not aspirin, reduce platelet thrombus formation in flowing blood exposed to atherosclerotic plaques, Thromb Haemost, 2007, pp. 435-443, vol. 97.
Phillips DR, et al., Therapeutic approaches in arterial thrombosis,, J Thromb Haemost, 2005, pp. 1577-1589, vol. 3.
Popma JJ, et al., Antithrombotic therapy during percutaneous coronary intervention: the Seventh ACCP Conference on Antithrombotic and Thrombolytic Therapy. Chest 126:576S-99S (2004).
Porter, et al. (eds ), a portion of "Coronary Amity Disease," Chapter 210 in The Merck Manual of Diagnosis and Therapy, 19th Edition, Merck & Co., Inc, Rahway, NJ, 2011, title pages and text pp. 2087-2110.
Price MJ, New antiplatelet therapies in development, Am J Health-Syst Pharm, 2008, pp. S11-S15, vol. 65.
Price, et al., Standard- vs High-Dose Clopidogrel Based on Platelet Function Testing After Percutaneous Coronary ntervention, JAMA, 2011, pp. 1097-1105, vol. 305, No. 11.
Raju NC, et al., J Platelet ADP-receptor antagonists for cardiovascular disease: past, present and future, Nat Clin Pract Cardiovasc Med, 2008, pp. 766-780, vol. 5, No. 12.
Revnefjord A, et al., Ongoing treatment with cangrelor, but not ticagrelor, is associated with a significant reduction in the efficacy of clopidogrel in an ex-vivo canine model, J Thromb Haemost, 2009, p. 349, vol. 7(Suppl 2).
Ravnefjord, et al., Evaluation of ticagrelor pharmacodynamic interactions with reversibly binding or non-reversibly Yinding P2Y(12) antagonists in an ex-vivo canine model, Thromb Res. Oct. 2012;130(4):622-8.
Rich J and Wiviott SD, New antiplatelet therapies for acute coronary syndromes, Curr Cardiol Rep, 2007, pp. 303-311, vol. 9.
Sabatine et al., Addition of clopidogrel to aspirin and fibrinolytic therapy for myocardial infarction with ST-segment alevation, N Engl J Med 2005; 356:1179-89.
Sabatine MS, Novel antiplatelet strategies in acute coronary syndromes, Clev Clin J Med, 2009, pgs. S8-S15, vol. 76 suppl 1).
Schneider, et al., Coronary Artery Disease Mar. 2009, vol. 20, No. 2, pp. 175-178.
Schornig A. et al., Ticagrelor-is there need for a new player in the antiplatelet-therapy field? N Engl J Med 361:1108-11 (2009).
Siddique A, et al., New antiplatelet drugs: beyond aspirin and clopidogrel, Int J Clin Pract, 2009, pp. 776-789, vol. 63.
Silber S, et al., Guidelines for percutaneous coronary interventions, The Task Force for Percutaneous Coronary nterventions of the European Society of Cardiology, Eur Heart J 26:804-47 (2005).
Steg, P. G. et al., Ticagrelor Versus Clopidogrel in Patients With ST-Elevation Acute Coronary Syndromes Intended for Reperfusion With Primary Percutaneous Coronary Intervention A Platelet Inhibition and Patient Outcomes (PLATO) Trial Subgroup Analysis, Circulation, 2010, pp. 2131-2141, vol. 122, No. 3.
Steinhubl S and Roe MT, Optimizing platelet P2Y12 inhibition for patients undergoing PCI, Cardiovasc Drug Rev, 2007, pp. 188-203, vol. 25, No. 2.
Stone G.W. et al., Bivalirudin for patients with acute coronary syndromes. N Engl J Med 355:2203-16 (2006).
Stone GW, et al., Paclitaxel-eluting stents versus bare-metal stents in acute myocardial infarction, N Engl J Med 360:1946-59 (2009).
Storey RF, Clinical experience with antithrombotic drugs acting on purine receptor pathways, Drug Dev Res, 2001, pp. 202-212, vol. 52.
Storey RF, et al., Comparison of the pharmacodynamic effects of the platelet ADP receptor antagonists clopidogrel and AR-C69931MX in patients with ischaemic heart disease, Platelets, 2002, pp. 407-413, vol. 13.
Storey RF, et al., Inhibition of ADP-induced p-selection expression and platelet-leukocyte conjugate formation by clopidogrel and the P2Y12 receptor antagonist AR-C69931 Mx but not aspirin, Thromb Res, 2002, pp. 488-494, vol. 38.
Storey RF, et al., Potential therapeutic effect of the novel platelet adenosine diphosphate receptor (P2T) antagonist, AR C69931MX, as assessed by in vitro studies in human whole blood. A possible adjunct to aspirin therapy?, Eur Heart J, 1998, p. 493, 19(SUPP):54.
Storey RF, et al., The central role of the P(2T) receptor in amplification of human platelet activation, aggregation, secretion and procoagulant activity, Br J Haematol, 2000, pp. 925-934, vol. 110.
Storey RF, New developments in antiplatelet therapy, Eur Heart J, 2008, pgs. D30-D37, 10 (Supp D).
Storey RF, et al., First clinical study of the novel platelet ADP receptor (P2T) antagonist AR-C69931MX, assessing safety, tolerability and activity in patients with acute coronary syndromes, Circulation, 1999, p. 1-170 vol. 100, No. 18.
Storey RF, The P2Y12 receptor as a therapeutic target in cardiovascular disease, Platelets, 2001, pp. 197-209, vol. 12.
Storey RF, Variability of response to antiplatelet therapy, Eur Heart J, 2008, pp. A21-A27, 10(SUPP A).
Storey RF, et al., Inhibition of Platelet Aggregation by AZD6140, A Reversible Oral P2Y12 Receptor Antagonist, Compared with Clopidogrel in Patients with Acute Coronary Syndromes, JACC, 2007, pp. 1852-1856, vol. 50, No. 19.
Straub A, et al., Evidence of Platelet Activation at Medically Used Hypothermia and Mechanistic Data Indicating ADP as a Key Mediator and Therapeutic Target, JAHA, 2011, pp. 1607-1016.
Gurbel PA, et al., Drug insight: Clopidogrel nonresponsiveness. Nature Clin Pract Cardiovasc Med 3: 387-95 (2006).
Testa L, et al., Current concepts on antiplatelet therapy: focus on the novel thienopyridine and non-thienopyridine agents, Advances in Hematology, 2010, 7 pages.
The article "What are the risks of percutaneous coronary intervention" (NHLBI, NIH. http://www.nhlbi.nih.gov/health/aealth-topics/topics/angioplasty/risks.html, Aug. 28, 2014.
The GUSTO Investigators. An international randomized trial comparing four thrombolytic strategies for acute myocardial infarction. N Engl J Med 329:673-82 (1993).
Thygesen K, et al., Universal definition of myocardial infarction, Circulation 116:2634-53 (2007).
Trissei, et al. Turbidimetric assessment of the compatibility of taxol with 42 other drugs during simulated Y-site injection, Am J Hosp Pharm, 49:1716-9 (1992).
Trissel LA, et al., Physical compatibility of melphalan with selected drugs during simulated Y-site administration, Am J Hosp Pharm 50:2359-63 (1993).
Ueno M, et al., Update on the clinical development of cangrelor. Expert Rev Cardiovasc, 2010, pp. 1069-1077, vol. 8L.
Van Giezen JJ, Optimizing platelet inhibition, Eur Heart J, 2008, pp. D23-D29, vol. 10(Suppl D).
Vasiljev KS, et al., 2-Alkylthio-substituted platelet P2Y12 receptor antagonists reveal pharmacological identity between the rat brain Gi-linked ADP receptors and P2Y12, Neurophanncol, 2003, pp. 145-154, vol. 45, No. 1.
Voisin, et al., Are P2Y12 Reaction Unit (PRU) and % Inhibition Index Equivalent for the Expression of P2Y12 Inhibition by the VerifyNow Assay? Role of Haematocrit and Haemoglobin Levels, Thromb. Haemost, 2011, pp. 227-229, vol. 106.
Wallentin L , et al., Ticagrelor versus clopidogrel in patients with acute coronary syndromsyndromes. N Engl J Med 361 1045-57(2009).

(56) References Cited

OTHER PUBLICATIONS

Wallentin, P2Y12 inhibitors: differences in properties and mechanisms of action and potential consequences for clinical use, European Heart Journal, 2009, pp. 1964-1977; published ahead of print Jul. 24, 2009.
Wang K, et al., Blockade of the Adp P2T receptor sustains coronary artery recanalization and improves the myocardium tissue perfusion in the canine thrombosis model, Circulation, 2001, p. 96, vol. 104 (17 Suppl).
Wang K, et al., Sustained coronary artery recanalization with adjunctive infusion of a novel P2T-receptor antagonist AR-C69931 in a canine model, JACC, 2000, pp. 281A-82A, vol. 35(2 Suppl).
Wang K, et al., Blockade of the platelet P2Y12 receptor by AR-C69931MX sustains coronary artery recanalization and mproves the myocardial tissue perfusion in a canine thrombosis model, Arterioscler Thromb Vase Biol, 2003, pp. 357-362, vol. 23, No. 1.
Weaver WD, et al., Intravenous AR C69931MX, a novel P2T platelet receptor antagonist, in patients undergoing percutaneous coronary interventions preliminary results from a placebo or active controlled trial, JACC, 2000, pp. 36A-37A, vol. 35 (2SupplA).
Weaver WD, et al., Safety and efficacy of a novel direct P2T receptor antagonist, AR C6991MX, in patients undergoing percutaneous coronary intervention, Eur Heart J, 2000, p. 382, vol. 21 (Suppl).
Windecker S, et al., Late Coronary Stent Thrombosis Circulation 116:1952-65 (2007).
Wiviott SD and De Lemos JA, Antiplatelet agents make a comeback in ST-elevation myocardial infarction, Am Heart J, 2007, pp. 603-606, vol. 154.
Wiviott SD, et al., Prasugrel versus clopidogrel in patients with acute coronary syndromes, N Engl J M ed 357:2001-15 (2007).
Wiviott SD, et al., Therapeutic goals for effective platelet inhibition: a consensus document, Rev Cardiovasc Med, 2006, pp. 214-225, vol. 7.
Xiang, B, et al., The P2Y12 Antagonists, 2Me SAMP and Cangrelor, Inhibit Platelet Activation through P2Y12/Gr-Dependent Mechanism, PLOS One, 2012, pp. 1-10, vol. 7, Issue 12.
Kumar, Gannu Praveen, et al.; Fundamentals and Applications of Lyophilization; Johrnal of Advanced Pharmaceutical Research. 2011,2(4), 157-169; ISSN: 2229-3787; Talia Padmavathi College of Pharmacy, Orus, Kareemabad, Warangal.
AstraZeneca LP, Wilmington, DE 19850; 2011, 2013, 2015; Highlignts of Prescribing Information—BRILINTA (ticagrelor) tablets, for oral use—Initial U.S. Approval 2011; 24 pages.
Rey, Louis and May, Joan C.; Freeze Drying/ Lyophilization of Pharmaceutical and Biological Products; Third Edition Drugs and the Pharmaceutical Sciences; vol. 206; Informa Healthcare; 98 pages.
Firstenberg, M.S., et al., P4-Safety and Efficacy of Cangrelor, An Intravenous, Short-Acting Platelet Inhibitor in Patients Requiring Cardiac Surgery, American Association for Thoracis Surgery, 2012.
Todd, Meredith; Cangrelor Versus Standard Therapy to Achieve Optimal Management of Platelet Inhibition. (Platform) History of Changes for Study: NCT00385138; ClinicalTrials.gov/archive (7 pages); U. S. National Library of Medicine.
NCT00767507 Clinical Trials.gov Archive, https://clinicaltrials.gov/archive/NCT00767507/2011/08/08, Aug. 5, 2011.
Abbrachio MP, et al., International union of pharmacology LVIII: update on the P2Y G protein-coupled nucleotide Yeceptors: from molecular mechanisms and pathophysiology to therapy, Pharmacol. Rev, 2006, pp. 281-341, vol. 58, No. 3.
Accumetric, LLC, VerifyNow User System User Manual, 2009.
Ahrens I and Bode C, Novel antiplatelet therapies following percutaneous coronary interventions, Curr Opin Investig Drugs, 2009, pp. 902-911, vol. 10.
Aleil B, et al., Flow cytometric analysis of intraplatelet VASP phosphorylation for the detection of clopidogrel resistance n patients with ischemic cardiovascular diseases, J Thromb Haemost, 2005, pp. 85-92.

Angiolillo DJ, ADP Receptor Antagonism. What's in the Pipeline?, Am J Cardiovasc Drugs, 2007, pp. 423-432. Vol. 7 No 6.
Angiolillo DJ, et al., Clinical overview of promising nonthienopyridine antiplatelet agents, Am Heart J, 2008, pp. S23-528, vol. 156, No. 2, Supp 1.
Angiolillo DJ, et al., Pharmacology of emerging novel platelet inhibitors, Am Heart J, 2008, pp. S10-S15, vol. 156, No. 2, Supp. 1.
Angiolillo DJ, et al., Randomized Comparison of a High Clopidogrel Maintenance Dose in Patients with Diabetes Mellitus and Coronary Artery Disease, Circulation, 2007, 708-716, 115.
Ansel et al., "Pharmaceutical Dosage forms and Drug Delivery Systems", Lippincott Williams and Wilkins, 1999, pp. 48-53.
Barker CM and Price MJ, Antiplatelet therapy in acute coronary syndromes, Curr Cardiol Rep, 2008, pp. 327-333, vol. 10, No. 4.
Bassand, J-P, Unmet needs in antiplatelet therapy, EHJ Supplements, 2008, pp. D3-D11, vol. 10, Supp. D.
Bavry et al., Appropriate use of drug-eluting stents: balancing the reduction in restenosis with the concern of late thrombosis, Lancet 2008, 371:2134-33.
Bavry et al. Benefit of early invasive therapy in acute coronary syndromes: a meta-analysis of contemporary Yandomized clinical trials J Am Coll Cardiol. Oct. 3, 2006; 48(7):1319-25.
Becker RC, Platelet surface physiology and its importance in pharmacotherapy design and development: The adenosine diphosphate receptor antagonists, J Thromb Thrombolysis, 2000, pp. 35-53.
Becker, RC, et al., Management of Platelet-Directed Pharmacotherapy in Patients with Atherosclerotic Coronary Artery Disease Undergoing Elective Endoscopic Gastrointestinal Procedures, JACC, 2009, pp. 2261-2276, vol. 54, No. 24.
Beers, et al., (eds.) "Coronary Artery Disease," Chapter 73 in the Merck Manual of Diagnosis and Therapy, 18th Edition, Merck & Co., Inc , Rahway, NJ, Jan. 2006, title pages and text pp. 626-652.
Bellemain-Appaix A, et al., New P2Y12 inhibitors versus clopidogrel in percutaneous coronary intervention. A metaanalysis, J Am Coll Cardiol, 2010, pp. 1542-1551, vol. 56.
Bhatt D.L, Intensifying platelet inhibition-navigating between Scylla and Charybdis. N Engl J Med 357:2078-81 (2007).
Bhatt DL, Prasugrel in clinical practice. N Engl J Med 361:940-2 (2009).
Bhatt DL, et al. Effect of platelet inhibition with cangrelor during PCI on ischemic events. N Engl J Med, 2013, pp. 1303-1313, vol. 368.
Bhatt DL, et al., Intravenous platelet blockade with cangrelor during PCI, N Engl J Med, 2009, vol. 361, pp. 2330-2341.
Bhatt DL, To Cath or Not to Cath That Is No. Longer the Question. JAMA. 2005;293(23):2935-2937.
Bhatt et al., Utilization of early invasive management strategies for high-risk patients with non-ST-segment elevation acute coronary syndromes: results from the CRUSADE Quality Improvement Initiative. JAMA. Nov. 3, 2004; 292 (17):2096-104.
Boeynaems JM, et al., P2Y receptor antagonists in thrombosis, Curr Opin Investig Drugs, 2005, pp. 275-282, vol. 6, Mo 3.
Bonello, et al., Consensus and Future Directions on the Definition of High On-Treatment Platelet Reactivity to Adenosine Diphosphate, JACC, 2010, pp. 919-933, vol. 56.
Brilakis, et al., Perioperative Management of Patients with Coronary Stents, JACC, 2007, vol. 49, pp. 2145-2150.
Buckland R, et al., Cangrelor inhibits the binding of clopidogrel and prasugrel active metabolites to the P2Y12 receptor, Eur Heart J, 2009, p. 193, vol. 30 (Suppl 1).
Buckland RJ,et al, Reversible binding of cangrelor to the P2Y12 receptor prevents the binding of clopidogrel and orasugrel active metabolites, J Thromb Haemost, 2009, p. 942, vol. 7 (Suppl 2).
Cattaneo M, Platelet P2 receptors: old and new targets for antithrombotic drugs, Expert Rev Cardiovasc Ther, 2007, pp. 45-55, vol. 5, No. 1.
Chattaraj SC, Cangrelor Astra Zeneca, Curr Opin Investig Drugs, 2001, pp. 250-255, vol. 2, No. 2.
Dhesebro J.H. et al., Thrombolysis in Myocardial Infarction (TIMI) Trial, Phase I: A comparison between intravenous tissue plasminogen activator and intravenous streptokinase. Clinical findings through hospital discharge. Circulation 76: 142-54(1987).

(56) References Cited

OTHER PUBLICATIONS

Christensen K, et al., Effects on blood compatibility in vitro by combining a direct P2Y12 receptor inhibitor and heparin coating of stents, Platelets, 2006, pp. 318-327, vol. 17, No. 5.

Cohen M, et al., Pharmacoinvasive management of acute coronary syndrome: incorporating the 2007 ACC/AHA Guidelines. The CATH (Cardiac Catherization and Antithrombotic Therapy in the Hospital) Clinical Consensus Panel Report-III, J Invasive Cardiology, 2007, pp. 525-540, vol. 19, No. 12.

Collet J.P et al., Cytochrome P450 2C19 polymorphism in young patients treated with clopidogrel after myocardial infarction: a cohort study. Lancet 373:309-17 (2009).

Cutlip D.E. et al., Clinical end points in coronary stent trials: a case for standardized definitions. Circulation 115:2344-51 (2007).

Dalal AR, et al., Brief review: coronary drug-eluting stents and anesthesia, Can J Anaest, 2006, pp. 1230-1243, vol. 53, No. 12.

De Bruyne et al., Fractional Flow Reserve—Guided PCI versus Medical Therapy in Stable Coronary Disease. N Engl J Med 2012, 367: 991-1001 [Erratum, N Engl J Med 2012, 367:1768].

Desai NR and Bhatt DL, The state of periprocedural antiplatelet therapy after recent trials, J Am Coll Cardiol Intv, 2010 pp. 571-83, vol. 3.

Diaz-Ricart M, Cangrelor tetrasodium, Drugs of the Future, 2008, vol. 33, No. 2, pp. 101-110.

Ding Z, et al., Identification of a potent inverse agonist at a constitutively active mutant of human P2Y12 receptor, Mol Pharmacol, 2005, pp. 338-345, vol. 69, No. 1.

Dovlatova et al., "Competition Between Reversible and Irreversible P2Y12 Antagonists and Its Influence on ADP-Mediated Platelet Activation," Journal of Thrombosis and Haemostasis, 5(Suppl. 2), Abstract No. S-340 (2007).

Dovlatova N, et al., Detection of P2Y(14) protein in platelets and investigation of the role of P2Y(14) in platelet function n comparison with the EP(3) receptor, Thromb Haemost, 2008, pp. 261-270, vol. 100.

Dovlatova NL, et al., The reversible P2Y12 antagonist cangrelor influences the ability of the active metabolites of clopidogrel and prasugrel to produce irreversible inhibition of platelet function, J Thromb Haemost, 2008, pp. 1153-1159, vol. 6.

Examination Report dated Aug. 21, 2013 in the related European Application No. 09747490.2.

Extended European Search Report dated Apr. 11, 2012 in the related European Application No. 09747490.2.

Extended European Search Report dated Apr. 8, 2015 in the related European Application No. 12824414.2.

Monagle, Paul et al., Thrombosis in children with BT shunts, Glenns and Fontans/Progress in Pediatric Cardiology. 2005, vol. 21, N.1, pp. 17-21.

Federal Service on Intellectual Property Federal Slate Budgetary Enterprise "Federal Institute of Industrial Property" (FIPS) Search Report for application No. 2019142647; Filed Jun. 22, 2018; dated Nov. 29, 2021.

\* cited by examiner

A.

B.

| | Fl$_{3004}$(mean ± SD) | % inhibition |
|---|---|---|
| Before | 112.80 ± 14.04 | 0 |
| During | 36.69 ± 3.38 | 67 |
| After | 113.26 ± 12.53 | 0 |

METHOD OF PREVENTING OF SYSTEMIC-TO-PULMONARY-ARTERY SHUNT THROMBOSIS

CROSS REFERENCE TO RELATED APPLICATIONS

This application claims priority to U.S. Ser. No. 62/524,102, filed on Jun. 23, 2017, the entire contents of which are hereby incorporated by reference in their entirety.

FIELD OF THE INVENTION

The invention pertains to the field of thromboprophylaxis and particularly to preventing stent thrombosis in pediatric patients, including neonates, and preventing shunt thrombosis in high risk patients undergoing systemic-to-pulmonary artery shunt surgery. Neonates with cyanotic congenital heart disease palliated with a systemic-to-pulmonary artery shunt are at high risk of thrombosis.

BACKGROUND OF THE INVENTION

Congenital heart defects (CHD) are the most common type of birth defect. It affects 8 out of every 1,000 newborns and has a wide range of disease severity. However, the majority of those born with structural heart anomalies are otherwise healthy, and corrective procedures may result in a normal lifespan (Monagle, 2005). While great technical advances have been achieved in palliative and corrective measures and in the care of critically ill neonates, these procedures are associated with an increased risk of acute thrombotic events (ATE) in this patient population (Monagle, 2004; Tormene et al., 2006; Monagle et al., 2008; Manlhiot et al., 2011).

Palliation with a modified BT shunt is indispensable for the management of a select group of neonates with cyanotic congenital heart disease. However, such patients are at high risk for thrombotic complications such as acute shunt occlusion, which remains a major source of morbidity and mortality. Although aspirin therapy, in general, is thought to reduce the risk of shunt occlusion and improve survival, it is typically not administered until 12 to 24 hours after surgery. A limited retrospective review of pediatric cardiac patients with evidence of shunt occlusion at Columbia University Medical Center revealed that the majority of cases occurred prior to the administration of an antiplatelet agent, establishing an unmet need for thromboprophylaxis during this vulnerable period.

Acute thromboembolic events (ATE) are rapidly becoming the new epidemic in centers that care for critically ill neonates due to an increase in invasive monitoring, lifesaving technologies such as extracorporeal membrane oxygenation (ECMO), and new surgical techniques and graft materials used to repair complex congenital heart disease. (Monagle P, Newall F, Barnes C, Savoia H, Campbell J, Wallace T, Crock C. "Arterial thromboembolic disease: a single-centre case series study." J Paediatr Child Health. 2008; 44:2832; Tormene D, Gavasso S, Rossetto V, Simioni P. "Thrombosis and thrombophilia in children: a systematic review." Semin Throm. Hemost. 2006; 32:724-728; Manlhiot C, Menjak I B, Brandão L R, Gruenwald C E, Schwartz S M, Sivarajan V B, Yoon H, Maratta R, Carew C L, McMullen J A, Clarizia N A, Holtby H M, Williams S, Caldarone C A, Van Arsdell G S, Chan A K, McCrindle B W. "Risk, clinical features, and outcomes of thrombosis associated with pediatric cardiac surgery." Circulation. 2011; 124:1511-1519; Chalmers E A. "Pediatric thrombosis." J Clin Pathol. 2000; 53:419-423.) In the latter case, infants (<6 months) constitute the major proportion (~70%) of patients seen in tertiary care centers with ATEs. (Monagle P. "Anticoagulation in the young." Heart. 2004; 90:808-812.) In particular, those with single ventricle physiology who require a systemic-to-pulmonary artery shunt placement (e.g. modified Blalock-Taussing or central shunts) are at greatest risk, especially in the early postoperative period. (Manlhiot C, Menjak I B, Brandão L R, Gruenwald C E, Schwartz S M, Sivarajan V B, Yoon H, Maratta R, Carew C L, McMullen J A, Clarizia N A, Holtby H M, Williams S, Caldarone C A, Van Arsdell G S, Chan A K, McCrindle B W. "Risk, clinical features, and outcomes of thrombosis associated with pediatric cardiac surgery." Circulation. 2011; 124:1511-1519; Fenton K N, Siewers R D, Rebovich B, Pigula F A. "Interim mortality in infants with systemic-to pulmonary artery shunts." Ann Thorac Surg. 2003; 76:152-156; Monagle Paul. "Thrombosis in children with B T shunts," Glenns and Fontans. Prog Pediatr Cardiol. 2005; 21:17-21; Al Jubair K A, Al Fagih M R, Al Jarallah A S, Al Yousef S, Ali Khan M A, Ashmeg A, Al Faraidi Y, Sawyer W. "Results of 546 Blalock-Taussig shunts performed in 478 patients." Cardiol Young. 1998; 8:486-490.) Consequently, this has resulted in suboptimal postoperative outcomes as exemplified in a retrospective review of 2,058 neonates who underwent palliation with a systemic-to-pulmonary artery shunt at multiple centers; discharge mortality and complication rates were around an aggregate of 6.7% and 12.3%, respectively. (Heidari-Bateni G, Norouzi S, Hall M, Brar A, Eghtesady P. "Defining the best practice patterns for the pediatric systemic-to-pulmonary artery shunt procedure." J Thorac Cardiovasc Surg. 2014; 147:869-873.) Early institution of aspirin, an irreversible inhibitor of platelet cyclooxygenase, within 12 hours of surgery has reduced the risk of shunt thrombosis and death in this patient population. (Al Jubair K A, Al Fagih M R, Al Jarallah A S, Al Yousef S, Ali Khan M A, Ashmeg A, Al Faraidi Y, Sawyer W. Results of 546 "Blalock-Taussig shunts performed in 478 patients." Cardiol Young. 1998; 8:486-490; Heidari-Bateni G, Norouzi S, Hall M, Brar A, Eghtesady P. "Defining the best practice patterns for the pediatric systemic-to-pulmonary artery shunt procedure." J Thorac Cardiovasc Surg. 2014; 147: 869-873; Li J S, Yow E, Berezny K Y, Rhodes J F, Bokesch P M, Charpie J R, Forbus G A, Mahony L, Boshkov L, Lambert V, Bonnet D, Michel-Behnke I, Graham T P, Takahashi M, Jaggers J, Califf R M, Rakhit A, Fontecave S, Sanders S P. "Clinical outcomes of palliative surgery including a systemic-to-pulmonary artery shunt in infants with cyanotic congenital heart disease: does aspirin make a difference?" Circulation. 2007; 116:293-297; Motz R, Wessel A, Ruschewski W, Bürsch J. "Reduced frequency of occlusion of aorto-pulmonary shunts in infants receiving aspirin." Cardiol Young. 1999; 9:474-477). However, there remains an urgent need for pharmacologic protection prior to the administration of an oral antiplatelet agent in order to minimize the period during which patients are vulnerable to an ATE.

Thienopyridines (e.g. clopidogrel) are a class of antiplatelet agents that target the ADP receptor P2Y12 and are known to reduce the risk of ischemia and thrombosis in adult patients during and after percutaneous coronary intervention (PCI). They do so by impairing P2Y12 potentiation of platelet dense granule secretion in response to strong agonists, stabilization of platelet aggregates by contributing to the activation of αIIbβ3, and inhibition of the antiplatelet effects of prostacyclin. Despite its proven clinical efficacy, clopidogrel has several major drawbacks that would limit it use during the vulnerable period for post-operative pediatric cardiac patients. These include the requirement for oral administration that may result in erratic absorption particularly in bypass cases, delay in the onset of action due to the need for conversion of the pro-drug to an active metabolite, and irreversible inhibition of $P2Y_{12}$ that would necessitate platelet transfusion(s) if bleeding occurred Interestingly, a previous clinical trial evaluating clopidogrel therapy in infants with cyanotic congenital heart disease palliated with a systemic-to-pulmonary-artery shunt failed to show any benefit in reducing the rate of death or shunt-related morbidity in drug treated patients. In the majority of cases, patients were also receiving aspirin therapy at the time of administration of clopidogrel. Of note, clopidrogrel is a prodrug that requires metabolism by the liver to generate its active form, which was unknown at the time that study was performed. It is also an irreversible inhibitor of the P2Y12 receptor. Target value for platelet inhibition in that trial was ~30% as determined by LTA. One major conclusion drawn from this study was that platelets from these young patients might be less responsive to agonists such as ADP as evidenced by the lower dose of clopidogrel needed to achieve similar levels of inhibition of platelet aggregation using LTA as compared to adults. This suggested that the P2Y12 signaling pathway may be developmentally regulated and/or of less importance in supporting thrombus generation in this population as compared to adults.

Cangrelor, an adenosine triphosphate (ATP) analogue, is a P2Y12 receptor antagonist given intravenously with properties more suitable for short-term use, which include a rapid, direct, predictable, and reversible inhibition of platelet function. It does not require conversion to an active form as compared to clopidogrel. It has a half-life of 3 to 6 minutes in adults with restoration of hemostasis, as assessed by bleeding time, seen within 10 minutes of cessation of infusion of a supratherapeutic dose and full platelet function recovery within 60 minutes as determined by response to ADP.

The alternatives forms and salts of cangrelor, processes for their production, and pharmaceutical compositions comprising them, are well known in the art and set forth, for example, in U.S. Pat. No. 5,721,219. Additional disclosure relevant to the production and use of cangrelor may be found in U.S. Pat. Nos. 5,955,447; 6,130,208; 6,114,313; 8,680,052; 759,316; 9,295,687; 9,427,448; 9,439,921; and 9,700,575.

Cangrelor is also rapidly inactivated by dephosphorylation to the nucleoside. On the basis of these characteristics, it was selected for clinical development as an IV antithrombotic agent and has recently been approved by the FDA for use in adults undergoing PCI.

Cangrelor may also have value as a potential bridging agent to oral therapy in neonates with cyanotic congenital heart disease who require palliation with a systemic-to-pulmonary-artery shunt.

Despite advances in adjunctive pharmacotherapy, there remains an urgent need for pharmacologic protection prior to the administration of an oral antiplatelet agent in order to minimize the period immediately after surgery during which patients, in particular the pediatric patients, are vulnerable to an acute thrombotic event (ATE).

We provide a pharmaceutical composition comprising a $P2Y_{12}$ inhibitor as anti-platelet agents for use in preventing and/or treating thrombosis, having pharmacological properties that are well suited for critically ill pediatric and pediatric patients with congenital heart disease requiring thromboprophylaxis.

SUMMARY OF THE INVENTION

The present invention is directed to a use of cangrelor in the treatment and/or prevention of shunt thrombosis in patients suffering congenital heart disease. Additionally, the present invention is directed to the use of cangrelor in the treatment and/or prevention of shunt or stent thrombosis in pediatric patients undergoing shunt surgery or stent implantation respectively. Another aspect of the invention provides a pharmaceutical composition comprising cangrelor for use in patients suffering congenital heart disease undergoing shunt surgery.

Another aspect of the invention provides a pharmaceutical composition comprising cangrelor for use in the treatment and/or prevention of shunt thrombosis in patients undergoing shunt surgery wherein the shunt surgery is selected from the group including systemic-to-pulmonary artery shunt, Blalock-Taussing shunt, central shunt, or right ventricle to pulmonary artery palliative shunts.

Another aspect of the invention provides a pharmaceutical composition comprising cangrelor for use in patients undergoing systemic-to-pulmonary artery shunt surgery.

Another aspect of the invention provides a pharmaceutical composition comprising cangrelor for use in the treatment and/or prevention of shunt or stent thrombosis in pediatric patients suffering congenital heart disease.

Another aspect of the invention provides a pharmaceutical composition comprising cangrelor for use in the treatment and/or prevention of shunt or stent thrombosis in pediatric patients undergoing shunt surgery or stent implantation surgery.

Another aspect of the invention provides a pharmaceutical composition comprising cangrelor for use in pediatric patients undergoing shunt surgery or stent implantation wherein the shunt surgery or stent implantation is selected from the group including systemic-to-pulmonary artery shunt, Blalock-Taussing shunt, central shunt, right ventricle to pulmonary artery palliative shunts, or ductus arterious stents.

Another aspect of the invention provides a pharmaceutical composition comprising cangrelor for use in pediatric patients wherein the pediatric patients suffer single ventricle physiology palliated with systemic-to-pulmonary artery shunt.

Another aspect of the invention provides a pharmaceutical composition comprising cangrelor for use in the treatment and/or prevention of shunt or stent thrombosis wherein the administration is intravenous. The patient population for shunt thrombosis prevention and/or treatment is adult and pediatric patients, including neonate. The patient population for stent thrombosis prevention and/or treatment is pediatric patients, including neonates.

Another aspect of the invention provides a pharmaceutical composition comprising cangrelor for use in the treatment and/or prevention of shunt or stent thrombosis wherein the method comprises:
i) performing the shunt surgery or stent implantation;
ii) administering the composition comprising cangrelor after surgery.

Another aspect of the invention provides a pharmaceutical composition comprising cangrelor wherein the composition is administered as a bolus, or as a continuous infusion, or as a bolus followed by a continuous infusion, or as a continuous infusion followed by a bolus.

Another aspect of the invention provides a pharmaceutical composition comprising cangrelor for the above indications, wherein the amount of cangrelor administered as continuous infusion is between about 0.1 and about 4 μg/kg/min. Preferably, the amount of cangrelor is between about 0.1 and 1.5 μg/kg/min, more preferably between about 0.1 and 1 μg/kg/min, even more preferably from about 0.1 and 0.5 μg/kg/min, where still more preferred amount is between about 0.1 and 0.3 μg/kg/min.

Another aspect of the invention provides a pharmaceutical composition comprising cangrelor for use as a bridging agent to oral antiplatelet therapies in pediatric patients undergoing shunt surgery or stent implantation.

Another aspect of the invention provides a pharmaceutical composition comprising cangrelor for use as a bridging agent to oral antiplatelet therapies in pediatric patients undergoing shunt surgery or stent implantation wherein the shunt surgery or stent implantation is selected from the group including systemic-to-pulmonary artery shunt, Blalock-Taussing shunt, central shunt, right ventricle to pulmonary artery palliative shunts or ductus arterious stents.

Another aspect of the invention provides a pharmaceutical composition comprising cangrelor for use as a bridging agent to oral antiplatelet therapies in pediatric patients undergoing shunt surgery or stent implantation, wherein the administration comprises:

i) administering a continuous infusion of cangrelor after shunt surgery or stent implantation for at least one hour or longer;
ii) discontinuing the treatment with cangrelor;
iii) administering the oral antiplatelet therapy.

Another aspect of the invention provides a pharmaceutical composition comprising cangrelor for use as a bridging agent wherein the continuous infusion of cangrelor is preferably carried out at a dosage as above defined.

Another aspect of the invention provides a pharmaceutical composition comprising cangrelor for use in preventing acute stent thrombosis in patients undergoing orthotopic heart transplant.

Another aspect of the invention provides a method of preventing shunt thrombosis in high risk pediatric patients undergoing systemic-to-pulmonary artery shunt surgery.

Another aspect of the invention is a method of preventing shunt thrombosis in a high risk patient undergoing systemic-to-pulmonary artery shunt surgery, the method comprising:

i) performing systemic-to-pulmonary artery shunt surgery and
ii) administering cangrelor immediately after surgery.

The high risk patient preferably is a pediatric patient, most preferably a neonate.

DETAILED DESCRIPTION OF THE DRAWINGS

FIG. 1. Time from surgery to shunt occlusion in pediatric cardiac patients. The data represent postoperative in-hospital population from 2013 to 2015. Dotted line denotes the time aspirin (ASA) is typically given by enteral route.

Figure 2:
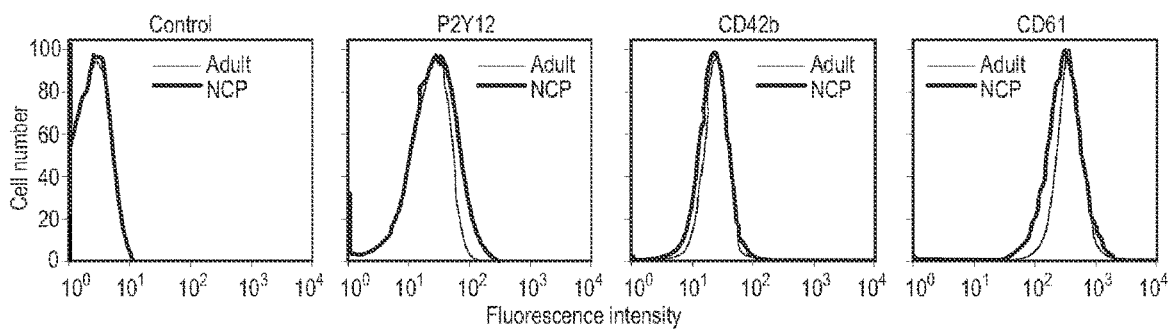
Figure 2:
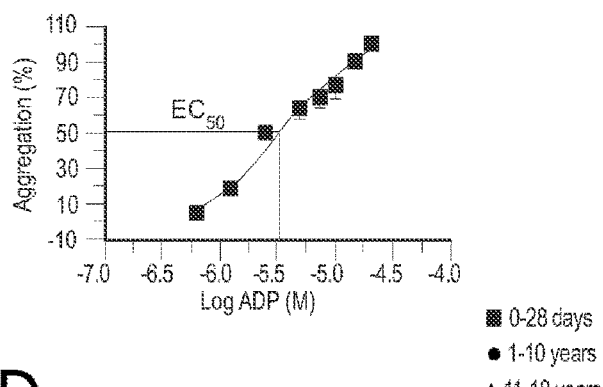
Figure 2:
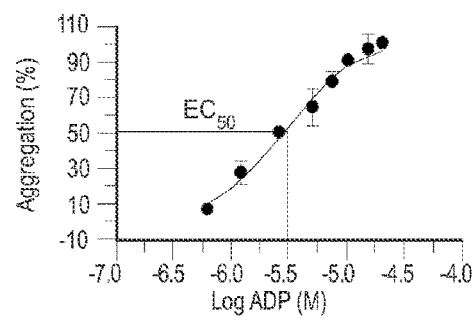
Figure 2:
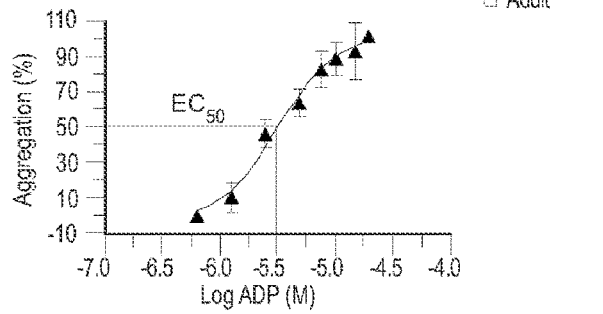
Figure 2:
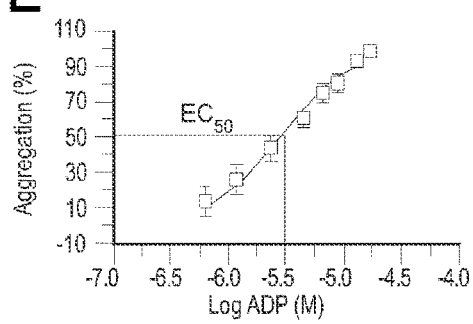

FIG. 2. P2Y12 receptor expression and ADP response of platelets. A representative flow cytometry histograms of antibody staining for the P2Y12 receptor on resting platelets isolated from pediatric cardiac patients (NCP) versus healthy adults (n=5 independent experiments). Histograms of antibody staining for GPIbα (CD42b) and integrin αIIbβ3 (CD61) are shown for comparison. B-E, Concentration response curves for the determination of EC50 values for ADP as measured by light transmission aggregometry (LTA) using purified platelets from pediatric and pediatric patients with congenital heart disease or healthy adult volunteers in the presence of fibrinogen. Results are the mean±SEM; n=4-6 individuals for each concentration of ADP tested.

Figure 3:
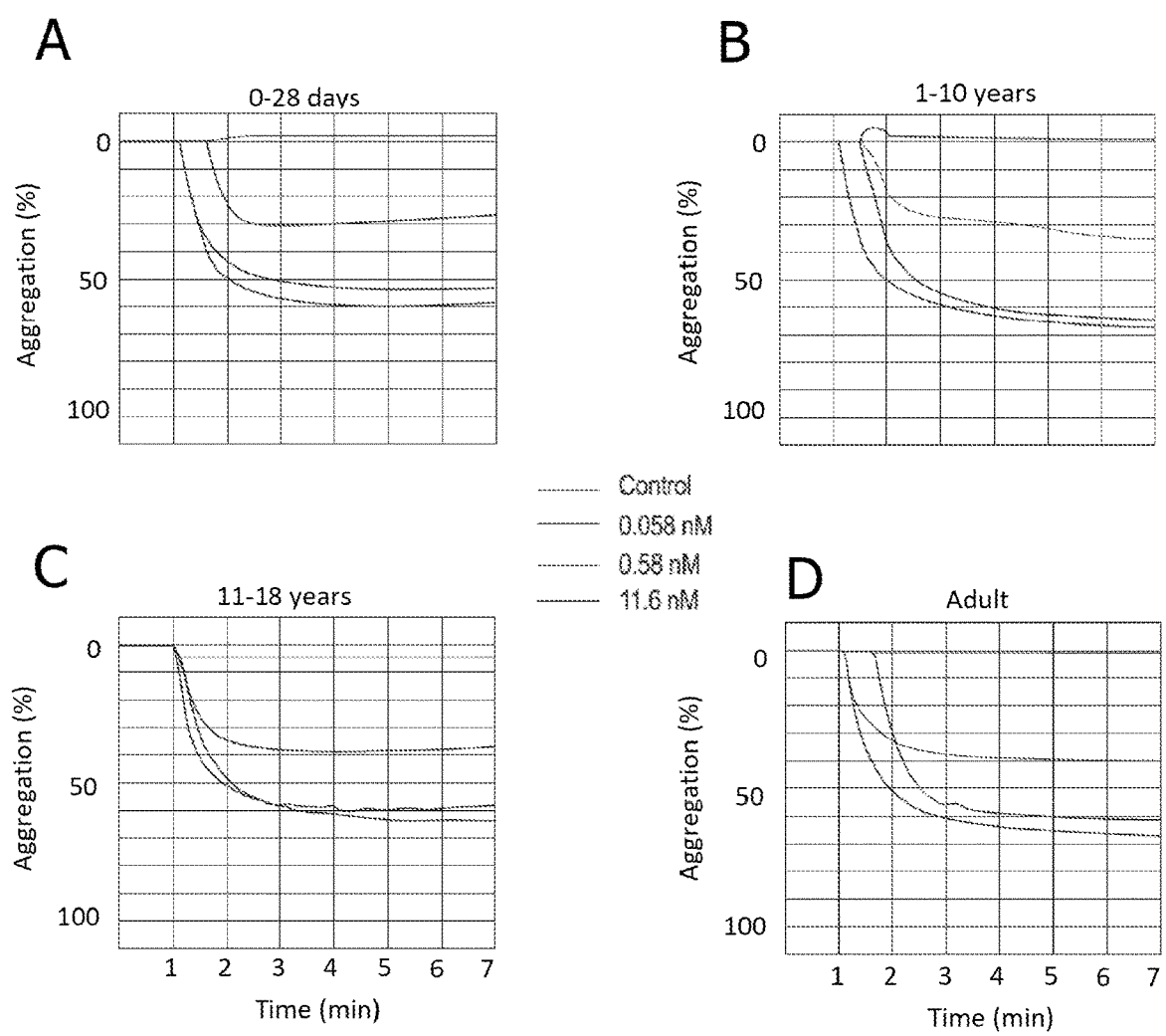

FIG. 3. Effect of cangrelor on platelet aggregation in response to ADP. A-D, Representative tracings of ADP (20 μM)-induced aggregation of platelets isolated from pediatric and pediatric patients with congenital heart disease or healthy adult volunteers in the presence of indicated concentrations of cangrelor.

Figure 4:
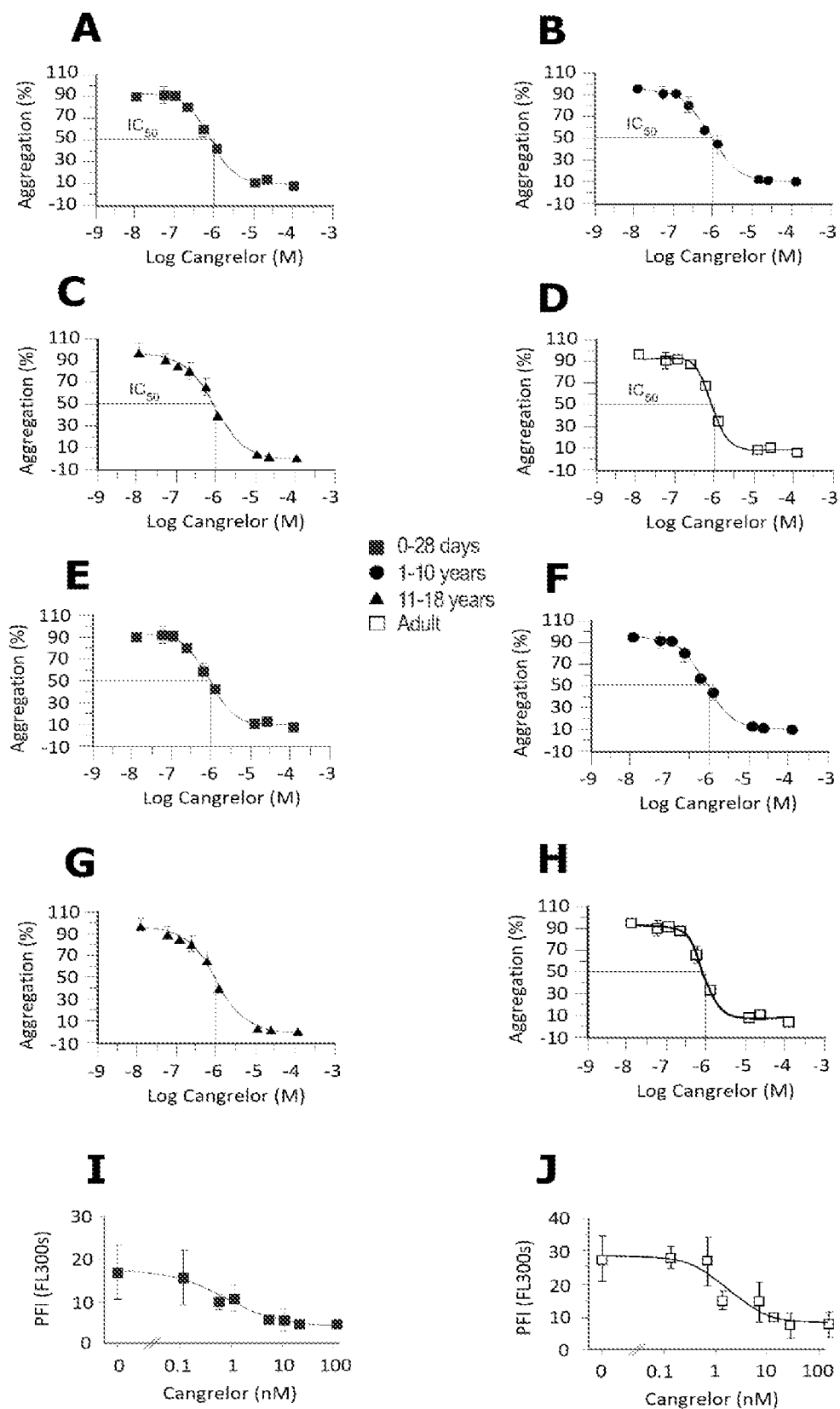

FIG. 4. IC50 curves for cangrelor using LTA and a microfluidic device. Concentration response curves for the determination of IC50 values for 20 μM ADP (A-D) and 5 μM ADP (E-H) as measured by LTA using purified platelets from pediatric and pediatric patients with congenital heart disease or healthy adult volunteers in the presence of fibrinogen. Data represent the mean±SEM. n=4-6 individuals for each concentration of antagonist tested. I-J, Concentration response curves for cangrelor under flow conditions. A microfluidic device containing a thrombogenic surface of collagen was used to determine IC50 values for cangrelor added to PPACK-treated whole blood from pediatric patients with single ventricle physiology (n=4; 38 separate clotting events) or healthy adults (n=7; 56 separate clotting events). Data represent the mean±SEM.

Figure 5:
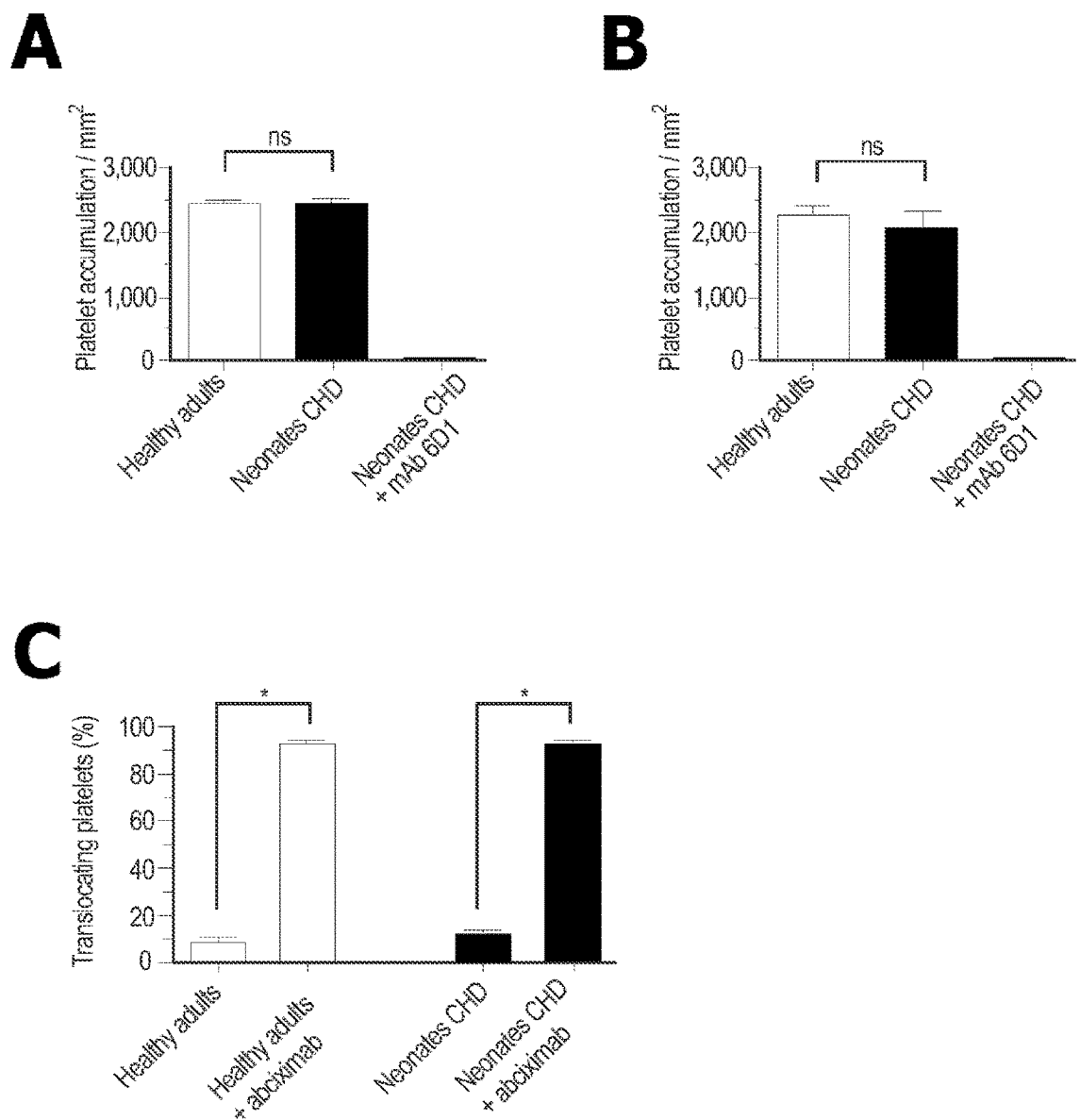

FIG. 5. Human platelet interactions with plasma VWF in flow. A, Accumulation of human platelets on surface-immobilized VWF obtained from mice possessing the human A1 domain (VWFHA1). Whole blood from pediatric patients with single ventricle physiology or healthy adults was infused over the reactive substrate for 3 min (wall shear rate of 1,600 s−1) before assessing the number of interacting platelets. mAb 6D1 is a function blocking antibody to VWF receptor on platelets GPIbα. C, The ability human platelets translocating on surface-immobilized mouse plasma VWFHA1 to undergo firm adhesion and arrest in response to ADP stimulation. Abciximab is a function blocking antibody to integrin αIIbβ3, which is required for firm adhesion. Data represent the mean±SEM (n=5 individuals per group).

Figure 6:
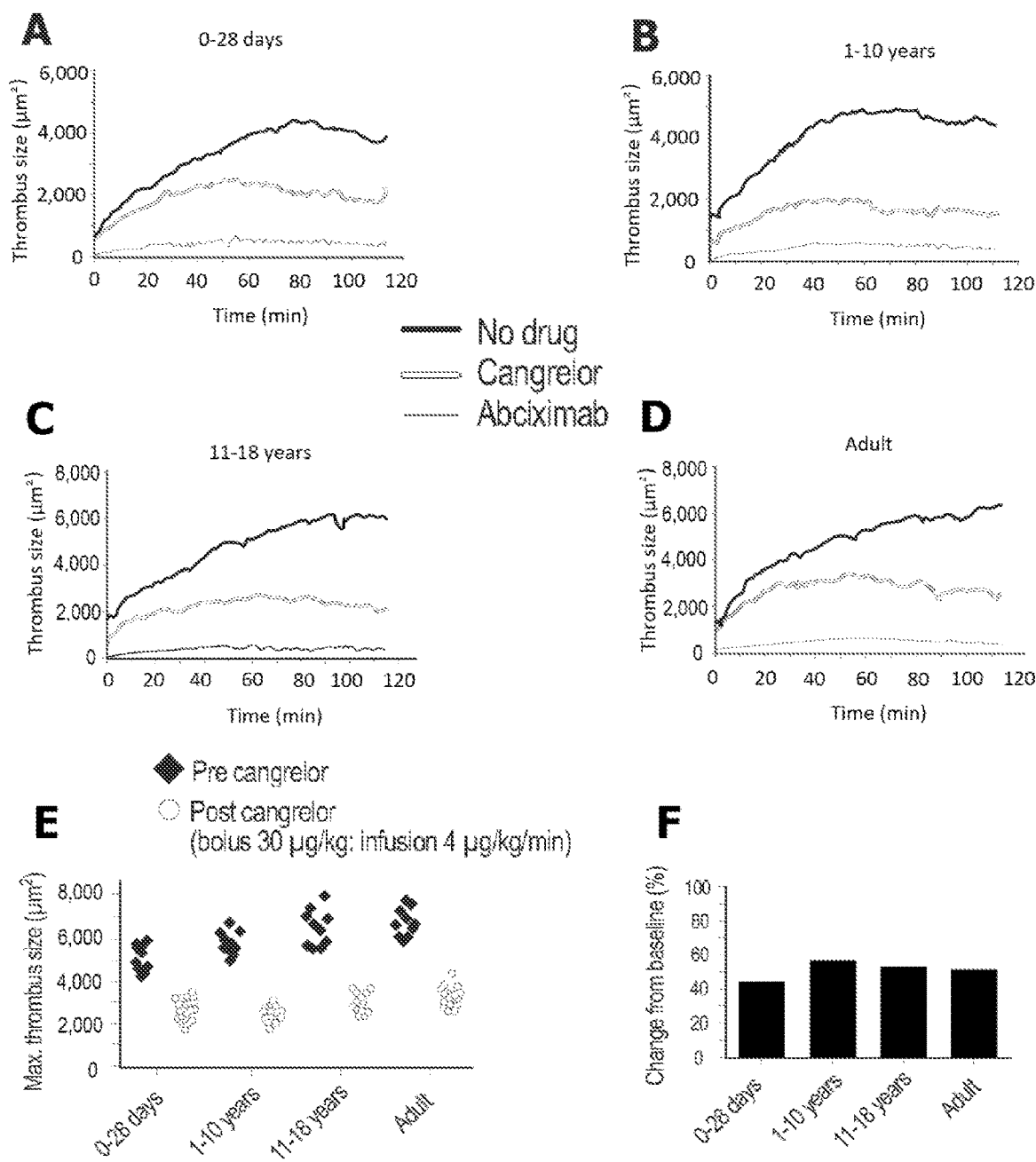

FIG. 6. Effect of cangrelor on human platelet thrombus formation in avatar mice. Time course of the average size of thrombi formed (A-D) and maximal thrombus size obtained (E) in laser-injured arterioles of VWFHA1 mutant mice pre- and post-administration of cangrelor (same animal). The effects of the αIIbβ3 inhibitor abciximab (0.25 μg/kg bolus; 0.125 μg/kg/min infusion) are shown for comparison (n=3 independent experiments for each age group). Each symbol (E) represents the area of a thrombus in 1 arteriole of a mouse. Results for cangrelor are the mean±SEM of 8 independent experiments performed for each age group of pediatric patients with CHD or healthy adult volunteers. F, Percent change in thrombus size in response to cangrelor treatment based on data shown in E. Data are from represent mean±SEM.

Figure 7:
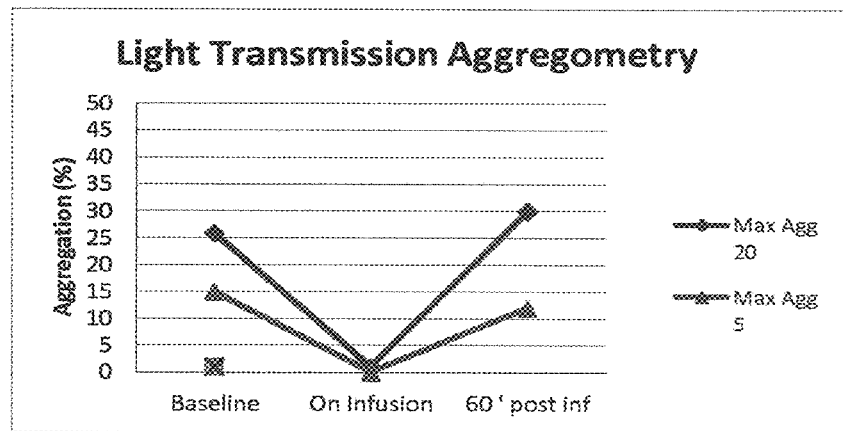
Figure 7:
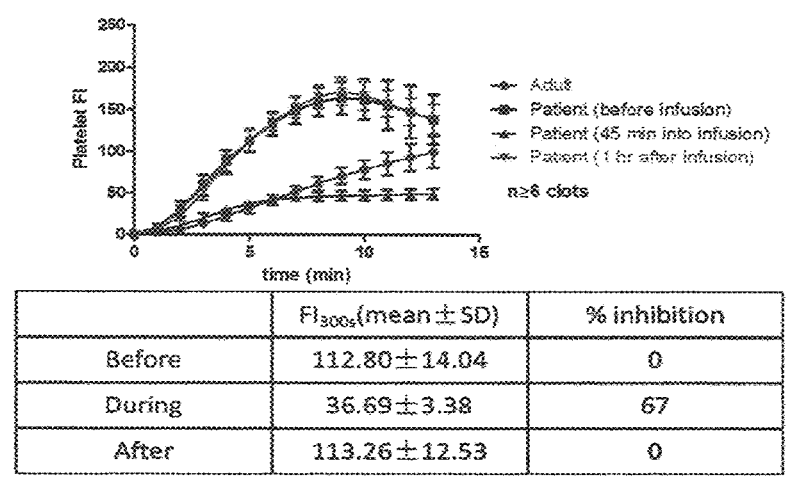

FIG. 7. Pharmacodynamic properties of cangrelor administered to neonates with CHD in the early post-operative period. A phase 1 clinical trial is currently being conducted to assess the drug plasma levels and effects on platelet aggregation using LTA and microfluidics. A, representative LTA results from a post-operative neonate with shunt placement 1 h prior to receiving cangrelor, 15 minutes prior to the end of the infusion (0.5 microgram/kg/min for 1 h), and 1 h after stopping the infusion of cangrelor. B, microfluidic results under the same conditions as outlined for LTA. Results are compared to a healthy adult who did not receive cangrelor.

DETAILED DESCRIPTION OF THE INVENTION

The present invention is directed to use of cangrelor for preventing and/or treating shunt thrombosis in a patient suffering congenital heart disease. In one embodiment, the patients are pediatric patients having cyanotic heart diseases.

The invention is thus directed to the use of cangrelor for preventing and/or treating shunt or stent thrombosis in a high-risk patient undergoing surgery for placement of palliative shunts or implantation of a stent. Typically, the surgery includes the placement of systemic to pulmonary shunts, Blalock-Taussing shunt, central shunts, right ventricle to pulmonary artery palliative shunts or ductus arterious stents. Advantageously according to the method of the present invention, the cangrelor is administered after surgery according to the above preferred embodiments, thus reducing the risk of acute thromboembolic events, particularly in pediatric patients.

As before reported, the patients undergoing the above mentioned shunt surgery or stent implantation, are at a high risk for thrombotic complications such as, without limitation, acute shunt occlusion, which remains a major source of morbidity and mortality.

It has to be noted that the well known and widely used aspirin therapy may help in reducing the risk of shunt occlusion, but it is typically not administered until 12 to 24 hours after surgery; therefore there is a vulnerable period immediately after surgery or implantation up to the administration of aspirin wherein the risk of onset of acute thromboembolic events is not managed. To date, there are no other antiplatelet therapies available that possess the desired characteristics of cangrelor, which include i.v. administration, rapid onset, rapid reversibility, and a form that does not require metabolic transformation for blockade of the P2Y12 receptor. These characteristics are ideal for this patient population that are both high risk for clot formation and bleeding in the early post-operative period.

The method of the present invention provides an efficacious method of treatment and/or prevention of thrombotic complications, particularly in pediatric patients, said method comprising the administration of cangrelor, shortly after the termination of the surgery, and in another embodiment, also in combination with an oral antiplatelet therapy. According to the invention, cangrelor is preferably administered intravenous by continuous infusion at a dosage, as above detailed, which is well suited, tolerated and safe also for pediatric patients.

In particular, the invention is directed to the use of cangrelor for prevention and/or treatment of shunt thrombosis in a high risk pediatric patients have single ventricle physiology undergoing systemic-to-pulmonary artery shunt surgery.

Definitions

In each aspect of the present invention, the term "cangrelor" encompasses the compound of Formula I, as well as tautomeric, enantiomeric and diastereomeric forms thereof, and racemic mixtures thereof, and pharmaceutically acceptable salts of these compounds, including a tetrasodium salt.

Formula I

In the present application, unless otherwise provided, the definition of pediatric patients includes individuals from birth to about 18 years, or a length-based weight (per Broselow Tape) of 36 kg or less. Patients who are known to be less than about 18 years of age but whose weight exceeds 36 kg may still be considered pediatric patients given their chronological age; however weights will then need to be estimated and adult dosages should be used. Thus, the pediatric patients includes e.g.: newborns up to about the first 28 days of life; newborns up to about 12 months; pediatric patients from: up to about 18 years; about 1 to about 3 years, from about 3 to about 5 years, from about 6 to about 10 years, from about 11 to about 14 years, and from about 14 to about 18 years.

Congenital heart defects (CHD) or congenital heart disease (CHD) are structural problems arising from abnormal formation of the heart or major blood vessels. At least 18 distinct types of congenital heart defects are recognized, with many additional anatomic variations. The word "congenital" means existing at birth. Congenital heart defects may be cyanotic or acyanotic.

Examples of common type of congenital heart disease are, but are not limited to: Aortic Valve Stenosis (AVS), Atrial Septal Defect (ASD), Coarctation of the Aorta (CoA), Complete Atrioventricular Canal defect (CAVC), d-Transposition of the Great Arteries, Ebstein's Anomaly, Hypoplastic Left Heart Syndrome, I-Transposition of the Great Arteries, Patent Ductus Arteriosus (PDA), Pulmonary Atresia, Pulmonary Valve Stenosis, Single Ventricle Defects, Tetralogy of Fallot, Total Anomalous Pulmonary Venous Connection (TAPVC), Tricuspid Atresia, Truncus Arteriosus, and Ventricular Septal Defect (VSD).

In the present description, unless otherwise provided, the definition of shunt surgery includes, but is not limited to: systemic-to-pulmonary artery shunts, Blalock-Taussing shunts, central shunts, or right ventricle to pulmonary artery palliative shunts.

In the present description, unless otherwise provided, the definition of stent implantation or stent surgery includes, but is not limited to ductus arterious stents.

DETAILED DESCRIPTION

In one aspect, the present invention demonstrates by means of standard LTA, high throughput microfluidic devices, and novel biological platforms that cangrelor is effective in preventing and treating thrombus formation in high risk pediatric populations suffering from congenital heart disease.

Platelet response to ADP and cangrelor was nearly identical for all age groups tested (P>0.05) based on calculated EC50 and IC50 values obtained by LTA.

The in vitro potency of cangrelor was further evaluated using whole blood from pediatric patients with single ventricle physiology and high throughput microfluidic assays, which yielded similar IC50 values. Consistent with these findings was the observation that platelets from pediatric patients expressed similar levels of the P2Y12 receptor as their adult counterparts.

To demonstrate the therapeutic utility of cangrelor in a biologically relevant model of thrombosis, we also evaluated the in vivo behavior of platelets from neonates and older patients with congenital heart disease in laser-injured arterioles of avatar mice (mice that have been genetically modified to support human platelet mediated hemostasis and thrombosis) before and immediately after drug administration. In all cases, cangrelor given at doses recommended for percutaneous coronary intervention (per 1 kg of body weight) reduced thrombus size by >45% thereby preventing vessel occlusion (P<0.0001).

To demonstrate the potential clinical utility of cangrelor, we first assessed the reactivity of platelets from neonates with cyanotic congenital heart disease, and in particular the contribution of the $P2Y_{12}$ receptor in supporting aggregation and thrombus formation.

By using standard as well as novel in vitro and in vivo based technologies, there were no significant differences in platelet response to either ADP-induced aggregation or cangrelor-mediated $P2Y_{12}$ receptor blockade for neonates and older pediatric patients with congenital heart disease as compare to healthy adults. In fact, $EC_{50}$ and $IC_{50}$ values, respectively, were nearly identical as determined by LTA using purified platelets.

As demonstrated in the present Experimental section, platelets from pediatric patients with cyanotic congenital heart disease have a nearly identical response to ADP and $P2Y_{12}$ receptor blockade as their adult counterparts. Cangrelor may prove to be an effective antithrombotic drug with pharmacological properties well suited for use in the immediate post-operative period for neonates palliated with a systemic-to-pulmonary artery shunts.

Although ex-vivo technologies such as flow cytometry, aggregometry, and microfluidic devices can yield important information concerning pediatric platelet function and drug response, they cannot fully replicate the complex adhesion and activation events critical for thrombus formation on the arterial side of the circulation. To address this issue, we utilized an avatar mouse model that better reflects the intravascular environment in humans by permitting human but not mouse platelets to support biologically relevant interactions at sites of vascular injury.

In fact, the power of this biological platform in assessing the antithrombotic properties of $P2Y_{12}$ inhibitors such as the thienopyridine derivative clopidogrel, was accomplished by evaluating the ability of platelets isolated from drug treated adults to support thrombus formation in laser-injured arterioles of these animals. Consistent with this dependency on the $P2Y_{12}$ receptor for maximal thrombus generation was the ability of cangrelor to limit the ability of platelets from neonates and older pediatric patients with congenital heart disease to support clot growth and vessel occlusion. Advantageously, cangrelor did not completely prevent platelet accumulation at sites of arteriole injury as compared to integrin αIIbβ3 inhibitor abciximab, which nearly abrogated platelet-vessel wall interactions.

A previous clinical trial evaluating the $P2Y_{12}$ inhibitor clopidogrel in infants with cyanotic congenital heart disease palliated with a systemic-to-pulmonary artery shunt failed to demonstrate any significant reduction in either mortality from any cause or shunt-related morbidity.

In addition to the prevention of shunt thrombosis, there may be other indications for the use of cangrelor in this high risk population. Despite an overall improvement in survival after a multistage palliative repair for hypoplastic left heart syndrome, patients may ultimately require an orthotopic heart transplant. However, it has been reported that as many as 25% of transplant patients will develop cardiac allograft vasculopathy necessitating coronary artery revascularization and stent placement as a short-term palliative solution. In fact, a recent study has suggested that PCI can be performed safely and effectively in this patient population, and has value as part of an evolving strategy to improve outcomes prior to re-transplantation. Cangrelor, which has been shown to significantly reduce ischemic events during PCI in adults with coronary artery disease without significantly increasing the risk of severe bleeding, may play a role in preventing acute stent thrombosis in these patients as well.

In one embodiment, the present invention is directed to the use of cangrelor for the treatment and/or prevention of acute stent thrombosis in pediatric patients undergoing or who have undergone orthotopic heart transplant. These patients typically need coronary artery revascularization and stent placement as a short-term palliative solution.

Given that shunt thrombosis remains a major cause of morbidity and mortality and that patients are at highest risk during the initially palliation for single ventricle physiology, we herein surprisingly present preclinical evidence that the non-thienopyridine $P2Y_{12}$ inhibitor cangrelor may fill a critical therapeutic void in thromboprophylaxis. This is justified based on the results reported in the present invention, demonstrating that platelets from pediatric patients with cyanotic congenital heart disease have a robust response to ADP and are surprisingly as amenable to $P2Y_{12}$ inhibition with cangrelor as their adult counterparts. Moreover, these findings are not restricted to pediatric shunt patients but appear to be independent of age and type of cardiac lesion.

Unique to this study is the ability to establish the in vivo efficacy of cangrelor using an avatar mouse model that permits the evaluation of human platelet interactions with the injured vessel wall, thus demonstrating that this $P2Y_{12}$ inhibitor yields the intended biological response.

In addition, in vitro data obtained from a phase 1 PK/PD clinical trial involving the infusion of cangrelor at 0.5 μg/kg/min or 0.25 μg/kg/min for one hour in post-operative neonates with CHD that required palliation with a systemic to pulmonary artery shunt demonstrated both the efficacy and rapid reversibility of cangrelor as assessed by LTA and microfluidics (FIG. 7).

The above nonclinical and clinical studies provide compelling evidence for an efficacious use of cangrelor in the prevention and/or treatment of shunt or stent thrombosis in patients suffering congenital heart disease who require palliation with a systemic to pulmonary artery shunt.

It is understood that all preferred groups or embodiments of the present invention described above may be combined with each other and apply as well mutatis mutandis.

In one aspect, the invention provides the use of cangrelor in the prevention and/or treatment of shunt thrombosis in patients suffering congenital heart disease undergoing shunt surgery. The treatment and/or prevention of shunt thrombosis in high risk patients undergoing shunt surgery comprises performing shunt surgery and administering cangrelor immediately after surgery.

In another aspect, the invention provides the use of cangrelor for the prevention and/or treatment of shunt or stent thrombosis in pediatric patients with cyanotic congenital heart disease palliated with a systemic-to-pulmonary artery shunt, Blalock-Taussing shunt, central shunt, right ventricle to pulmonary artery palliative shunts, and ductus arterious stents, wherein the pediatric patients are at high risk for thrombotic complications. The thrombotic complications or acute thromboembolic events such as acute shunt occlusion remain a major source of morbidity and mortality.

In a preferred embodiment, the invention provides the use of cangrelor for prevention and/or treatment of shunt thrombosis in a high risk pediatric patients undergoing systemic-to-pulmonary artery shunt surgery. The pediatric patients have single ventricle physiology.

In another aspect, the invention provides the use of cangrelor for prevention and/or treatment of stent thrombosis in a high risk pediatric patients palliated with a ductus arterious stents.

In another aspect, the invention provides the use of cangrelor to reduce the incidence and/or prevent the mortality in high-risk patients undergoing a shunt surgery, wherein mortality may be associated with acute thrombotic events. The high-risk patients are pediatric patients with congenital heart disease. In particular, the pediatric patients have single ventricle physiology.

In another aspect, the invention provides the use of cangrelor to reduce the incidence and/or prevent the mortality in high-risk pediatric patients undergoing a stent surgery, wherein mortality may be associated with acute thromboembolic events. The high-risk patients are pediatric patients with congenital heart disease.

The invention also provides pharmaceutical composition comprising cangrelor for the administration once or according to a dosing regimen wherein a number of doses are administered at varying intervals of time for a given period of time.

Administration of pharmaceutical compositions comprising cangrelor may be accomplished according to patient needs, for example oral, sublingual, intranasal, intraocular, rectal, transdermal, mucosal, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids).

Any known device useful for parenteral injection or infusion of drug formulations can be used in the methods of the present invention.

In a preferred embodiment of the invention, the administration is via parenteral, more preferably intravenous administration, via a peripheral IV or central venous line.

When administered intravenously, the pharmaceutical composition comprising cangrelor may be administered as a bolus, as a continuous infusion, as a bolus followed by a continuous infusion, or as a continuous infusion followed by a bolus.

In one embodiment the invention provides a pharmaceutical composition comprising cangrelor wherein the point in time when the pharmaceutical composition is administered is between about a half an hour and about 24 hours from the termination of the shunt surgery or stent implantation, such as at least about half an hour, about 1 hour, about 2 hours, about 3 hours, about 4 hours, about 5 hours, about 6 hours, about 7 hours, about 8 hours, about 9 hours, and about 10 hours or longer from the termination of the shunt surgery or stent implantation. Preferably, the administration is after at least about 1 hour, more preferably in a period of time comprised between about 2 and about 4 hours from the termination of the shunt surgery or stent implantation.

Preferably, the pharmaceutical composition comprising cangrelor is administered as continuous infusion. For example, the pharmaceutical composition according to the invention may be administered after the shunt surgery or stent implantation as a continuous infusion for at least about 10 minutes to about 72 hours. Preferably, the administration continues for at least about 1 hour, about 2 hours, about 3 hours, about 4 hours, about 5 hours, about 6 hours, about 7 hours, about 8 hours, about 9 hours, or about 24 hours or longer. More preferably, the infusion continues for at least about 10 minutes to about 2 hours; still more preferably, the infusion continues for at least one hour, or for a short period of time such as less than about an hour, such as about 15 minutes, about 30 minutes or about 45 minutes depending for example on the dosage, the age or the weight of the patients.

When the pharmaceutical composition comprising cangrelor is administered as a bolus,
it is administered within a short period of time, such as about two minutes or less, or about one minute or less, after shunt surgery or stent implantation.

In one aspect of the present invention, cangrelor can be administered before, during, and/or after shunt surgery or stent implantation.

When administered as a bolus, cangrelor is administered at dosage between about 5 µg/kg and about 100 µg/kg, preferably between about 5 µg/kg and about 40 µg/kg, even more preferably between about 10 µg/kg and about 35 µg/kg, still more preferably between about 10 µg/kg and about 30 µg/kg. For example, the pharmaceutical composition comprising cangrelor is administered at about 5 µg/kg, about 10 µg/kg, about 15 µg/kg, about 20 µg/kg, about 25 µg/kg, or about 30 µg/kg.

In one embodiment, an intravenous dose of up to about 4 microgram/kg/min, can be administered about 2 to about 4 h after shunt surgery or stent implantation and continued until the preferred time of administration of an oral agent.

The composition may be administered once, twice, thrice or more times a day.

In a further embodiment, the pharmaceutical composition comprising cangrelor is administered once the acute thromboembolic event is recognized or diagnosed, or at the onset of symptoms of the acute thromboembolic event.

For example, the pharmaceutical composition may be administered when symptoms of acute thromboembolic event are observed. The pharmaceutical composition is administered within a short period of time from the onset of symptoms of acute thromboembolic event.

The short period of time may range from about one or about two minutes to about one or about two hours.

In some embodiments, the method comprises administering the pharmaceutical
composition comprising cangrelor as a prophylaxis against an acute thromboembolic event.

Patients appropriate for such prevention include pediatric cardiac subjects who are undergoing shunt surgery or stent implantation for placement of systemic-to pulmonary artery palliative shunts (e.g., Blalock-Taussig or central shunt), right ventricle to pulmonary artery palliative shunts, or ductus arteriosus stents who are at risk of thrombotic events after repair of structural congenital heart disease.

In another aspect, the present invention provides the administration of pharmaceutical composition comprising cangrelor for the treatment of shunt or stent thrombosis in pediatric patients undergoing stent implantation or shunt surgery concurrently or sequentially (before or after) with at least one additional therapeutic agent.

The additional therapeutic agent may be, for example without limitation, a P2Y12-receptor inhibitor such as an oral P2Y12-receptor inhibitor, a glycoprotein IIb/IIIa inhibitor, aspirin and heparin. Administering an oral antiplatelet therapies, either concurrently or sequentially with the pharmaceutical composition comprising cangrelor in pediatric patients undergoing shunt surgery or stent implantation may also transition the patient to chronic or maintenance treatment with the antiplatelet inhibitor.

As mentioned above, the present invention also provides the use of cangrelor as a bridging agent to oral antiplatelet therapies in pediatric patients requiring a palliative systemic-to-pulmonary artery shunt, Blalock-Taussing shunt, central shunt, right ventricle to pulmonary artery palliative shunt or ductus arterious stent.

In one embodiment, the cangrelor is useful for transitioning pediatric patients from administration of cangrelor after shunt surgery or stent implantation to administration of a chronic or maintenance treatment with oral antiplatelet therapies, i.e. oral P2Y12, or aspirin.

In a preferred embodiment, the pharmaceutical composition comprising cangrelor is administered in a method comprising:
 i) administering a continuous infusion of cangrelor after shunt surgery or stent implantation for at least half an hour to about 72 hours;
 ii) discontinuing the treatment with cangrelor; and
 iii) administering the oral antiplatelet therapy.

In a further embodiment, the use of cangrelor in a method for transitioning pediatric patients from administration of cangrelor after shunt surgery or stent implantation to administration of a chronic or maintenance treatment with oral antiplatelet therapies includes a continuous infusion of cangrelor after shunt surgery or stent implantation at a dosage according to the above indicated preferred ones.

Cangrelor can be administered alone or combined with various pharmaceutically acceptable excipients.

The pharmaceutical composition of the present invention comprises cangrelor, and may further comprise one or more pharmaceutically acceptable excipients.

These pharmaceutical compositions may comprise one or more pharmaceutically acceptable excipients including, but not limited to, carriers, diluents, stabilizing agents, solubilizing agents, surfactants, buffers, antioxidants, preservatives, tonicity agents, bulking agents, lubricating agents, emulsifiers, suspending or viscosity agents, fillers, disintegrating agents, binding agents, wetting agents, antibacterials, antibiotics, antifungals, chelating agents, sweeteners, perfuming agents, flavoring agents, coloring agents, administration aids, and combinations thereof.

Particular excipients include, but are not limited to, cornstarch or gelatin, lactose, sucrose, dextrose, microcrystalline cellulose, kaolin, mannitol, sorbitol, dicalcium phosphate, sodium chloride, alginic acid, croscarmellose sodium, sodium starch glycolate, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, cyclodextrin or cyclodextrin derivatives (including HPCD ((2-hydroxypropyl)-cyclodextrin) and (2-hydroxyethyl)-cyclodextrin), hydrophilic and hydrophobic carriers, and combinations thereof.

Hydrophobic carriers include, for example, fat emulsions, lipids, PEGylated phospholipids, polymer matrices, biocompatible polymers, liposphere, vesicles, particles, and liposomes. In certain embodiments, the pharmaceutical compositions may comprise polyols, such as sorbitol, lactose, sucrose, inositol or trehalose.

The pharmaceutical compositions of the present invention may be formulated for the route by which they are administered to the patients, which include solids, liquids, and suspensions. For example, if the pharmaceutical composition is formulated for IV administration, the pharmaceutical composition may comprise an intravenous fluid, which includes, but is not limited to, water-for-injection (WFI), physiological saline, 0.9% NaCl, phosphate buffered saline, 5% dextrose in water, and 0.002% polysorbate 80 in water or Ringer's™ solution.

Such compositions may comprise cangrelor in an amount of about comprised between 0.10 and 200 μg/mL.

If the pharmaceutical composition is formulated for intramuscular administration, the pharmaceutical composition may comprise an intravenous fluid, which includes, but is not limited to, WFI, physiological saline, 0.9% NaCl, phosphate buffered saline, and 5% dextrose in water.

If the pharmaceutical composition is formulated for oral administration, the pharmaceutical composition may comprise excipients that include, but are not limited to diluents (e.g., sodium and calcium carbonate, sodium and calcium phosphate, and lactose), binding agents (e.g., acacia gum, starch, gelatin, sucrose, polyvinylpyrrolidone (Povidone), sorbitol, tragacanth, methylcellulose, sodium carboxymethylcellulose, hydroxypropyl methylcellulose, and ethylcellulose), fillers (e.g., calcium phosphate, glycine, lactose, maize-starch, sorbitol, or sucrose), wetting agents, lubricating agents (e.g., metallic stearates, stearic acid, polyethylene glycol, waxes, oils, silica and colloidal silica, silicon fluid or talc), disintegrating agents (e.g., potato starch, corn starch and alginic acid), flavouring agents (e.g. peppermint, oil of wintergreen, fruit flavoring, bubblegum, and the like), and coloring agents.

Excipients may also include coatings such as glyceryl monostearate or glyceryl distearate, to delay absorption in the gastrointestinal tract. For oral use, the pharmaceutical composition may be made in the form of a tablet, capsule, suspension or liquid syrup or elixir, wafers and the like.

The pharmaceutical compositions of the present invention may be prepared by admixing cangrelor with the one or more pharmaceutically acceptable excipients. Methods of admixing and devices useful for admixing are known in the art.

In certain embodiments, cangrelor and the one or more pharmaceutically acceptable excipients are dissolved and then admixed. The resulting mixture may be dried, such as through lyophilization, to form a solid pharmaceutical composition, or the resulting mixture may remain in solution form as a liquid pharmaceutical composition. In some embodiments, the solid pharmaceutical composition may be solubilized in an intravenous fluid before administration, for example, as a bolus or infusion.

In some embodiments, the pharmaceutical composition is prepared by dissolving and admixing cangrelor, mannitol, sorbitol, and optionally sodium hydroxide, and then lyophilizing the mixture. Prior to administration, the lyophilized mixture is dissolved in an intravenous fluid such as WFI or physiological saline.

The following examples illustrate the invention, without any limitation.

EXPERIMENTAL PART

Methods

Reagents

ADP and type 1 collagen (ChronoPar) were obtained from Chronolog (Havertown, Pa.). Human fibrinogen was purchased from Sigma Co. (Saint Louis, Mo.) and abciximab (ReoPro) from Centocor, Inc (Marvin, Pa.). The polyclonal anti-VWF antibody and Alexa 488 conjugated antihuman CD61 (GPIIIa) antibody were purchased from Dako (Carpinteria, Calif.) and Bio-Rad (Raleigh, N.C.; clone Y2/51), respectively. MAb 6D1 (function blocking antibody to human GPIbα) and cangrelor (P2Y12 inhibitor) were kindly provided by Barry Coller (Rockefeller University, N.Y.) and The Medicine Company (Parsippany, N.J.).

Mice $VWF^{HA1}$ mutant animals were generated and backcrossed 10 generations on a 129/SvJ background as previously described. All procedures performed on animals were approved by The Institutional Animal Care and Use Committees at Columbia University Medical Center.

Patient Population

Blood samples from 78 patients with CHD (neonates to 18 years) and healthy adults were collected to assess platelet reactivity and response to cangrelor using light transmission aggregometry (LTA), collagen-coated multichannel microfluidic devices, and genetically modified mice that support human but not mouse platelet-mediated thrombosis (avatar mouse). Patients were eligible for enrollment in the study if they were 0 to 18 years of age and with known congenital heart disease. Exclusion criteria included coagulation defects, known congenital or genetic conditions expected to affect platelet function, body weight <3 kg for pediatric patients and <6 kg for older pediatric patients, cardiopulmonary instability necessitating urgent or emergent surgical/catheter-based intervention, medications or other conditions that might significantly affect platelet function.

Seventy-eight pediatric patients with congenital heart disease were enrolled in this study. Three different study population groups were chosen (Table 1).

TABLE 1

Baseline Demographic Characteristics of Cardiac Patients

| Baseline Characteristics | 0-28 days | 1-10 years | 11-18 years |
|---|---|---|---|
| No. | 39 | 31 | 8 |
| Mean age | 12.8 | 4.1 | 15.3 |
| Female, % patients | 23.1 | 54.8 | 37.5 |
| Ethnicity, % patients | | | |
| Hispanic/Latino | 20.5 | 25.8 | 12.5 |
| Race, % patients | | | |
| White | 56.4 | 64.5 | 62.5 |
| Black | 7.6 | 6.5 | 12.5 |
| Asian | 15.5 | 3.2 | 12.5 |
| Native American | 0 | 0 | 0 |
| Other | 20.5 | 25.8 | 12.5 |
| Mean gestational age (weeks) | 38 | | |
| Diagnosis, % patients | | | |
| Hypoplastic left heart syndrome | 23.1 | 19.4 | 0 |
| Pulmonary atresia with intact ventricular septum | 0 | 3.2 | 0 |
| Tricuspid atresia | 0 | 6.5 | 0 |
| Transposition of great arteries | 33.3 | 12.9 | 0 |
| Tetralogy of Fallot | 2.6 | 19.4 | 25 |
| Double-inlet left ventricle | 5.1 | 3.2 | 0 |
| Double-outlet right ventricle | 0 | 3.2 | 12.5 |
| Coarctation | 12.8 | 3.2 | 12.5 |
| PDA | 0 | 12.9 | 0 |
| ASD | 0 | 0 | 25 |
| Heterotaxy | 7.7 | 0 | 0 |

The first included full-term neonates (0-28 days) with a body weight of ≥3 kg scheduled for cardiac surgery involving cardiopulmonary bypass. Of these, 56.4% were white, 7.6% were black, 15.5% were Asian, 20.5% were of Hispanic/Latino ethnicity, and 23.1% were female. Patients with single ventricle pathology accounted for 23.1% of the population enrolled in the study, with D-transposition of the great arteries accounting for the majority of patients (33.3%). During this period of time, ~23% of neonates requiring palliation with a systemic-to-pulmonary shunt had evidence of shunt occlusion necessitating a surgical intervention and/or rapid response ECMO. Interestingly, all events occurred within 24 hours of surgery with the majority of cases prior to initiation of aspirin therapy, FIG. 1.

The second group included pediatric patients ranging in age from 1-10 years (mean of 4.1 years) scheduled to undergo left heart catheterization for diagnostic or therapeutic purposes; the third group included adolescent patients ranging in age from 11-19 years (mean of 15.3 years) also undergoing left heart catheterization.

Blood Collection

For studies involving patients with congenital heart disease, blood was obtained from a central venous catheter after clearing the line of heparin; blood from healthy adult volunteers was obtained via routine venipuncture. In the majority of cases, 3.8% trisodium citrate served as anticoagulant. For microfluidic studies, whole blood was collected in a syringe containing the thrombin inhibitor H-D-Phe-Pro-Arg-chloromethylketone (PPACK, Calbiochem, San Diego, Calif.) to achieve a final concentration of 100 μM. Generation of PRP or purified platelets was performed by centrifugation as previously described.

Example 1

Platelet Aggregation Evaluation by Means of Light Transmission Aggregometry (LTA)

In this Example, platelet reactivity and response to cangrelor of pediatric patients and healthy adults was examined.

Purified platelets were suspended to a final concentration of 400,000/μl in platelet buffer containing 145 mM NaCl, 10 mM Hepes, 0.5 mM $Na_2HPO_4$, 5 mM KCl, 2 mM $MgCl_2$, 1 mM $CaCl_2$, 0.1% glucose, pH 7.4. Stock solutions of cangrelor were prepared on the day of experimentation and added to platelet suspensions (37γC, 1,200 rpm) 10 min prior to inducing aggregation with ADP (5 μM or 20 μM). Human fibrinogen (final concentration 200 μg/ml) was added to the platelet suspensions just prior to activation. Aggregation was assessed using a Chronolog Lumi-Aggregometer (model 540 VS, Chronolog, Havertown, Pa.) and permitted to proceed for 6 min after the addition of agonist. The results are reported as maximum percent change in light transmittance from baseline with platelet buffer used as a reference.

Results
Response of Platelets to ADP

Conflicting results exists regarding the overall reactivity of platelets from neonates with cyanotic congenital heart disease as compared to their healthy counterparts and adults, especially in response to physiologically relevant agonists such as ADP. It was also unclear whether platelets from this high risk population are as amenable to inhibition with antithrombotic drugs such the $P2Y_{12}$ receptor antagonists as those from adults.

To address these therapeutically relevant concerns, we first evaluated the level of expression of the $P2Y_{12}$ receptor on platelets isolated from neonates with cyanotic congenital heart disease. In comparison to platelets from adults, no discernible difference in $P2Y1_2$ surface expression was detected (FIG. 2A); similar results were obtained for the platelets receptors for VWF (GPIbα) and fibrinogen (αIIbβ3), which are indispensable for clot formation.

We next determine the functional response of platelets from neonates as well as older patients with congenital heart disease to ADP stimulation. This was accomplished by calculating $EC_{50}$ values for the agonist using isolated platelets in fibrinogen-supplemented buffer.

FIG. 2 (B through E) shows the mean (±SEM) percent platelet aggregation as a function of ADP concentration. Calculated $EC_{50}$ values were not significantly different for all age groups tested with mean values (±SEM) ranging from 2.9±0.1 μmol/L to 3.4±0.1 μmol/L (Table 2, P<0.001).

TABLE 2

$EC_{50}$ and $IC_{50}$ Values for ADP and Cangrelor, respectively

| Platelets | Adult | 0-28 days | 1-10 years | 11-18 years |
|---|---|---|---|---|
| $EC_{50}$ ± SEM (μmol/L) | 3.2 ± 0.2 | 3.4 ± 0.1 | 2.9 ± 0.1 | 3.2 ± 0.2 |
| $IC_{50}$ ± SEM* (nmol/L) | 0.82 ± 0.3 | 0.82 ± 0.2 | 0.79 ± 0.2 | 0.85 ± 0.2 |
| $IC_{50}$ ± SEM** (nmol/L) | 0.66 ± 0.3 | 0.74 ± 0.3 | 0.68 ± 0.3 | 0.76 ± 0.2 |

*= 20 μM ADP,
**= 5 μM ADP

Effect of Cangrelor on Platelet Aggregation

Cangrelor has been shown to be a potent inhibitor of ADP-induced platelet aggregation in adults. To date, no information exists on its ability to effectively mitigate the ADP response of platelets from neonates with congenital heart disease. To this end, we calculated IC50 values for this P2Y12 receptor antagonist using low and high concentrations of ADP (5 μM versus 20 μM). Consistent with results obtained by flow cytometry and in ADP-induced platelet aggregation studies, no statistical difference was observed in the amount of cangrelor needed to achieve half-maximal inhibition at either concentration of agonist (FIG. 3A through D (20 μM ADP), FIG. 4A through D (20 μM ADP), FIG. 4E through H (5 μM ADP); Table 1, P<0.001). Similarly results were observed for older populations of patients with congenital heart disease.

Example 2

Platelet Adhesion in Flow Evaluation of Neonates with Single Ventricle Physiology Using Multichannel Microfluidic Device In this Example, the platelet adhesion of neonates with single ventricle physiology was examined by means of multichannel microfluidic device.

A parallel-plate flow chamber was used to assess platelet accumulation on surfaceimmobilized plasma VWF at a wall shear rate of 1,600 $s^{-1}$. In brief, a polyclonal anti-VWF antibody was absorbed overnight (4° C.) to a six-well tissue culture plate. Subsequently, the plate was washed and non-specific interactions blocked by the addition of TBS containing 3% BSA, pH 7.4 (30 min, 37° C.). Human or murine (VWFHA1) plasma obtained from heparinized whole blood was added and the plates placed at 37° C. for an additional hour prior to use. Citrated whole blood was then perfused over the reactive substrate for 3 minutes, followed by the addition of platelet buffer lacking CaCl2 for 1 min. The number of platelets attached per unit area was determined by offline analysis (ImagePro Plus, Media Cybernetics Bethesda, Md.) of recorded digital images. For GPIba inhibition studies, mAb 6D1 (10 μg/ml) was added to anticoagulated human blood for 10 min before use.

Microfluidic devices with 8 individual channels (250 μm wide×60 μm-high) were fabricated in polydimethylsiloxane (PDMS) as previously described. The device was reversibly vacuum-sealed to a glass slide with its flow channels aligned perpendicularly to a patterned type 1 collagen surface (1 mg/ml). To visualize platelet accumulation over time, an Alexa Fluor 488 conjugated, non-function blocking mouse anti-human CD61 (GPIIb/IIIa) antibody was added (1:50 ratio) 7 min prior to performing experiments (0.125 μg/ml final concentration).

Whole blood from neonates with single ventricle pathology or healthy adults was perfused over the prothrombotic surface at an initial wall shear rate of 100 $s^{-1}$ by withdrawal from a single outlet into a syringe pump (Harvard Apparatus Pump 11 Elite, Holliston, Mass.). Platelet accumulation was visualized (10× objective lens) using an automated inverted microscope system (DMI6000, Leica) equipped with a CCD camera (DFC365FX, Leica). A custom stage insert held three microfluidic devices allowing replicate testing of four conditions. Images were captured in 30 s intervals for a total of 5 min. Platelet fluorescence intensities, which are directly proportional to the total platelet mass were measured and analyzed with Image J software (Image J; NIH, Bethesda, Md.). The center 65% of the prothrombotic region was selected for analysis to avoid edge effects. The initial image was taken as background and subsequent images were background corrected. Platelet adhesion and aggregate formation was not observed upstream or downstream of the collagen trip prior to full channel occlusion.

Calculation of Half Maximal Inhibitor Concentration and Cangrelor Sensitivity

Background-corrected fluorescence values were fitted with a 4 parameter dose-response model.

$$FI = A + \frac{A - B}{1 + 10^{[(\log IC_{50} - C) \times D]}}$$

where C represents the Cangrelor concentration; FI, the background-corrected fluorescence of 15 the corresponding region of interest; A and B, the minimum and maximum intensities, respectively; and D, the Hill coefficient. The data was fitted by a log (inhibitor) vs. response routine in GraphPad Prism 5.00 (GraphPad Software, La Jolla, Calif.).

Results

Further evidence supporting the in vitro potency of cangrelor in reducing the aggregation of platelets from neonates with single ventricle physiology was provided in microfluidic studies that recreate the hemodynamic conditions of thrombosis. Whole blood collected in PPACK was treated with various concentrations of cangrelor and then perfused over surface-immobilized collagen. In each experiment, 8 simultaneously forming thrombi per device were imaged in real time. Fluorescently labeled platelets were observed to accumulate only at the site of collagen exposure, with minimal non-specific upstream or downstream adhesion. Determination of surface fluorescence at 300 s ($FI_{300s}$) permitted calculation of effective $IC_{50}$ values, which were 0.69 nM and 0.95 nM for neonates with CHD versus healthy adults, respectively (FIGS. 4I and J).

Example 3

In Vivo Thrombus Formation Evaluation from Pediatric and Older Patients with Congenital Heart Disease Administration of anesthesia, insertion of venous and arterial catheters, fluorescent labeling of human platelets, and surgical preparation of the cremaster muscle in 12 week old male VWF HA1 mice have been previously described.

Human platelets (700K/µL) were continuously infused (25 µl/min) through a catheter placed in the ipsilateral femoral artery 2 min prior to and during laser-induced injury to ensure a level of circulating cells equivalent to humans. Injury to the vessel wall of arterioles (40-65 µm diameter) was performed with a pulsed nitrogen dye laser applied through a 20× water immersion Olympus objective. Human platelet-vessel wall interactions were visualized by fluorescence microscopy using a system equipped with a Yokogawa CSU-22 spinning disk confocal scanner, iXON EM camera, and 488-nm laser line (Revolution XD, Andor Technology, South Windsor, Conn.) to detect Calcein-AM-labeled cells, respectively. The extent of thrombus formation was assessed for 3 min after injury and the maximal area (µm2) of coverage determined by off-line analysis (ImagePro Plus, Media Cybernetics, Bethesda, Md.).

After establishing a baseline for normal thrombus generation in injured arterioles, cangrelor was then given initially as an intravenously bolus (30 µg/kg) and then as a continuous infusion (4 µg/kg/min) as described in previously clinical trials.

A minimum of 5 mice per patient group were studied (2 and 4 arterial segments pre and post-cangrelor per mouse, respectively).

Statistics

To compare mean thrombus areas between different treatment groups, we fit linear mixed models with random intercepts for each study animal. Linear mixed models permit comparison of mean differences between treatment groups while also considering the effect of the clustering of the data on the SEs resulting from multiple measurements obtained from each mouse used in intravital studies. In the case of platelet aggregation studies, values are presented as mean±SEM. A 2-tailed Student t test was used for comparisons between control conditions and treatments. Differences with values of $P<0.05$ were considered statistically significant.

Results

In Vivo Efficacy of Cangrelor

Previously, we have shown the preclinical utility of an avatar mouse model that preferentially supports human and not mouse platelet-mediated hemostasis and thrombosis.

This switch in species specificity for platelets resulted from the incorporation of the R1326H single mutation into the A1 domain of mouse VWF ($VWF^{R1326H}$), and more recently by replacement of the entire domain with its human counterpart (VWFHA1).

Of note, VWF mutant animals have a profound bleeding phenotype due to the inability of mouse platelets to stably interact with damaged vascular endothelium. As human platelet interactions with VWF is key to the initiation of thrombus formation in this avatar mouse model, we first evaluated the ability of platelets from neonates with CHD to accumulate on surface-immobilized human or murine $VWF^{HA1}$ under arterial flow conditions. Importantly, platelets from former accumulated on plasma VWF from humans or $VWF^{HA1}$ mutant mice at levels comparable to those from healthy adults (FIGS. 5A and B). Moreover, no significance difference was observed in the number of platelets from neonates that attached to either substrate (2,432±55 platelets/mm$^2$ versus 2,223±156 platelets/mm$^2$, respectively; $P=0.84$). Importantly, this interaction could be inhibited by the addition of the monoclonal antibody 6D1 that blocks the ability of the platelet receptor GPIbα to interact with the A1 domain of VWF.

Although GPIbα initiates platelet deposition at arterial shear rates, this adhesive interaction is labile in nature permitting platelets to translocate in response to forces generated by flowing blood. Ultimately it is the platelet integrin receptor αIIbβ3 that stabilizes adhesion by engaging with ligands such as VWF in response to ADP and/or thrombin. Consistent with this scenario is the ability of abciximab, an inhibitor of human αIIbβ3, to prevent the firm adhesion of platelets from pediatric patients with CHD or healthy adults to surface-immobilized VWF in response to ADP-induced activation in flow (FIG. 5C).

After establishing that plasma $VWF^{HA1}$ supports attachment as well as ADP-induced firm adhesion, we next set out to determine the potential therapeutic effect of cangrelor in preventing human platelet mediated thrombus in vivo. The dose and route of administration of the drug was based on previous clinical trials in adults undergoing PCI.

Fluorescently labeled human platelets were infused continuously through a catheter inserted into the femoral artery and their behavior in response to laser-induced arterial injury monitored before and after administration of cangrelor. Consistent with the requirement for ADP to promote a second wave of aggregation, $P2Y_{12}$ receptor blockade on platelets from pediatric cardiac patients yielded a ~45% reduction in thrombus size ($P<0.0001$) (FIGS. 6 A through F; see Table III).

TABLE III

| Age group | Contrast estimate | Standard error | P-value |
|---|---|---|---|
| 0-28 days | 2,261 | 224 | <0.0001 |
| 1-10 years | 3,314 | 224 | <0.0001 |
| 11-18 years | 3,475 | 224 | <0.0001 |
| Adult | 3,501 | 224 | <0.0001 |

Linear mixed model comparing average human platelet thrombus size (µm2) in VWFHA1 mutant mice. The contrast column is the mean difference between thrombus size pre- and post-administration of cangrelor for each age group tested. Standard errors and statistics were obtained from fitting of the linear mixed model.

By contrast, administration of abciximab abrogated platelet accumulation by >90% ($P<0.0001$). Similar results were obtained using platelets from older patients with congenital heart disease and healthy adults.

Various changes could be made in the above methods without departing from the scope of the invention as defined in the claims below. It is intended that all matter contained in the above description, and as shown in the accompanying figures, shall be interpreted as illustrative and not as limiting.

The invention claimed is:

1. A method of treating or preventing shunt thrombosis in a patient comprising administering a pharmaceutical composition comprising cangrelor to the patient, wherein the patient is a pediatric patient suffering from congenital heart disease.

2. The method of claim 1 wherein the patient is undergoing shunt surgery or stent implantation.

3. The method of claim 2 wherein the shunt surgery or stent implantation is selected from the group consisting of systemic-to-pulmonary artery shunt, Blalock-Taussing shunt, central shunt, right ventricle to pulmonary artery palliative shunt, and ductus arterious stent.

4. The method of claim 3 wherein the patients suffer single ventricle physiology palliated with systemic-to-pulmonary artery shunt.

5. The method of claim 1 wherein the administration is intravenous.

6. The method of claim 1 wherein the intravenous administration is a continuous infusion.

7. The method of claim 6 wherein the amount of cangrelor administered is between about 0.1 and about 4 µg/kg/min.

8. The method of claim 7 wherein the amount of cangrelor administered is between about 0.1 µg/kg/min and about 1.5 µg/kg/min.

9. The method of claim 8, wherein the point in time when the pharmaceutical composition is administered is between about half an hour and about 24 hours from the termination of the shunt surgery or stent implantation.

10. The method of claim 9, wherein the point in time when the pharmaceutical composition is administered is between about 2 and about 4 hours from the termination of the shunt surgery or stent implantation.

11. The method according to claim 1 further comprising: i) performing a shunt surgery or stent implantation; and ii) wherein the administering the pharmaceutical composition is after the shunt surgery or stent implantation.

12. The method according to claim 11 wherein the composition is administered as a bolus, or as a continuous infusion, or as a bolus followed by a continuous infusion, or as a continuous infusion followed by a bolus.

13. The method according to claim 11 wherein the composition is administered as a continuous infusion for at least about 10 minutes to about 72 hours or until administration of an oral agent for prevention of platelet aggregation.

14. The method according to claim 13 wherein the composition is administered as a continuous infusion for at least about 10 minutes to about 2 hours.

15. A method of treatment of a patient comprising administering a pharmaceutical composition comprising cangrelor to the patient wherein the patient is undergoing shunt surgery or shunt implantation and then administering oral antiplatelet therapies to the patient wherein the patient is a pediatric.

16. The method of claim 15 wherein the shunt surgery or stent implantation is selected from the group consisting of systemic-to-pulmonary artery shunt, Blalock-Taussing shunt, central shunt, right ventricle to pulmonary artery palliative shunt, and ductus arterious stent.

17. The method of claim 16 further comprising: i) the administering a continuous infusion of cangrelor after shunt surgery or stent implantation for at least one hour or longer; ii) discontinuing the treatment with cangrelor; and iii) administering the oral antiplatelet therapy.

18. The method of claim 17 wherein the continuous infusion of cangrelor is at dosage between about 0.1 and about 4 µg/kg/min.

19. The method of claim 18 wherein the continuous infusion is between about 0.1 and about 1.5 µg/kg/min.

20. The method of claim 18 wherein the continuous infusion is between about 0.1 and about 1 µg/kg/min.

21. The method of claim 18 wherein the continuous infusion is between about 0.1 and about 0.5 µg/kg/min.

22. The method of claim 18 wherein the continuous infusion is between about 0.1 and about 0.3 µg/kg/min.

* * * * *